(12) United States Patent
Kurtz et al.

(10) Patent No.: US 8,101,127 B2
(45) Date of Patent: Jan. 24, 2012

(54) FLUID DISINFECTION APPARATUS

(75) Inventors: Mark E. Kurtz, Ft. Lauderdale, FL (US); Scott P. Russell, Rutland, VT (US)

(73) Assignee: Ultravation, Inc., Poultney, VT (US)

( * ) Notice: Subject to any disclaimer, the term of this patent is extended or adjusted under 35 U.S.C. 154(b) by 561 days.

(21) Appl. No.: 12/070,029

(22) Filed: Feb. 14, 2008

(65) Prior Publication Data

US 2008/0138254 A1 Jun. 12, 2008

Related U.S. Application Data

(63) Continuation of application No. 10/504,044, filed on Aug. 4, 2004, now abandoned.

(51) Int. Cl.
*A62B 7/08* (2006.01)
*A61L 9/00* (2006.01)

(52) U.S. Cl. .............................. 422/121; 422/120; 422/5

(58) Field of Classification Search .................. 422/120, 422/121, 5; 96/224; 313/17
See application file for complete search history.

(56) References Cited

U.S. PATENT DOCUMENTS

| | | | | |
|---|---|---|---|---|
| 2,233,280 A * | 2/1941 | Barnes | ............................ | 362/319 |
| 3,098,611 A * | 7/1963 | Connell | ............................ | 40/714 |
| 3,275,818 A * | 9/1966 | Campbell | ................ | 362/249.01 |
| 3,541,322 A * | 11/1970 | Bennett | ........................ | 362/121 |
| 3,569,691 A * | 3/1971 | Tracy | ............................. | 362/233 |
| 3,637,342 A * | 1/1972 | Veloz | ............................. | 250/436 |
| 4,096,379 A * | 6/1978 | Taylor | ............................ | 362/235 |
| 4,367,410 A * | 1/1983 | Wood | ............................. | 250/431 |
| 4,482,809 A * | 11/1984 | Maarschalkerweerd | ...... | 250/436 |
| 4,995,181 A * | 2/1991 | Wolf | ............................... | 40/714 |
| 5,057,978 A * | 10/1991 | Conti | ............................. | 362/125 |
| 5,471,063 A * | 11/1995 | Hayes et al. | .................. | 250/436 |
| 5,590,390 A * | 12/1996 | Maarschalkerweerd | ... | 422/186.3 |
| 5,700,083 A * | 12/1997 | Boechel | ...................... | 362/249.1 |
| 5,902,552 A * | 5/1999 | Brickley | ........................ | 422/121 |
| 7,419,642 B2 * | 9/2008 | Fowler et al. | ................. | 422/121 |

* cited by examiner

*Primary Examiner* — Sean E Conley
*Assistant Examiner* — Regina M. Yoo
(74) *Attorney, Agent, or Firm* — Law Offices of Kenneth F. Dusyn; Kenneth F. Dusyn

(57) ABSTRACT

A fluid disinfection module (10) comprises a first housing (12) and a second housing (20) arranged in spaced-apart relationship to each other. The first housing (12) includes tubular support members (28) and (28*a*) extending laterally therefrom for respective slidable mateable engagement with corresponding tubular support members (30) and (30*a*) also laterally extending from second housing (20), to vary the lateral distance x between the first and second housings (12) and (20). A locking device maintains tubular support members (28,28*a*) and (30,30*a*) in fixed relationship with respect to each other.
First housing (12), second housing (20), and corresponding tubular support members (28,28*a*) and (30,30*a*) define a framework for supporting one or more ultraviolet radiation sources (18) and (26) that are detachably mounted at one end thereof to housings (12) and (20), respectively. Each of radiation sources (18) and (26) is preferably encased within a quartz sleeve (60), and communicates with one or more ballasts (80) disposed within or without their respective housings (12)(20) for supplying electricity to the radiation sources (18)(26).

27 Claims, 16 Drawing Sheets

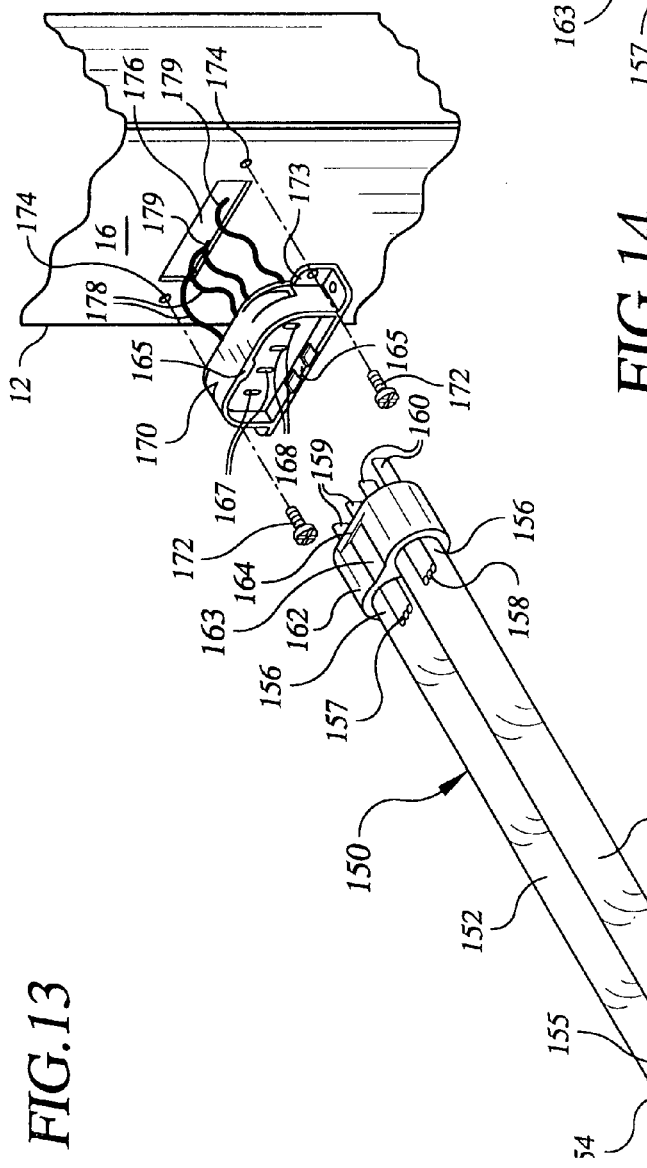
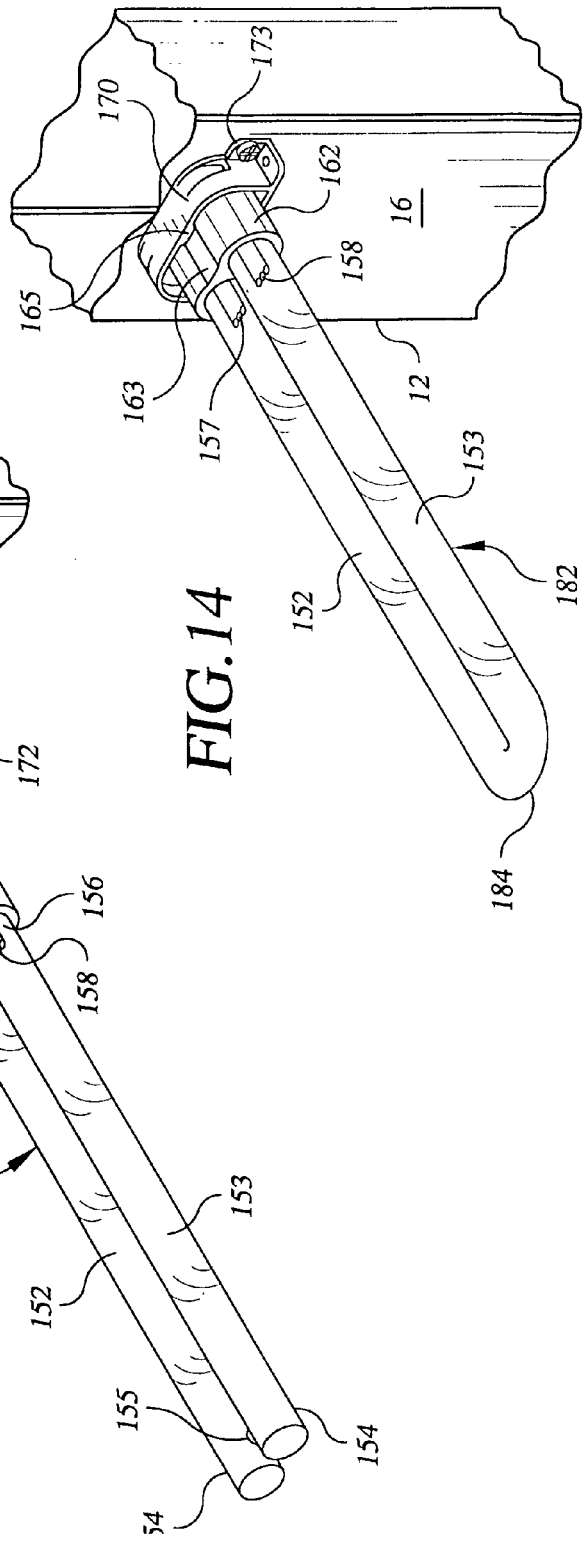
FIG.13
FIG.14

FLUID DISINFECTION APPARATUS

This is a continuation application claiming priority to application Ser. No. 10/504,044 filed Aug. 4, 2004.

BACKGROUND OF THE INVENTION

1. Field of the Invention

The invention broadly relates to a fluid disinfection apparatus utilizing an ultraviolet radiation source. More specifically, the invention provides an air disinfection module utilizing a plurality of ultraviolet lamps for incorporation into a heating/ventilation air conditioning ("HVAC") duct to disinfect the air passing therethrough.

2. Related Art

U.S. Pat. No. 4,872,980 discloses a plurality of ultraviolet lamps encased in protective quartz sleeves supported at their ends by rigid frame legs. One of the legs is hollow and receives lead wires connected to the lamps through openings spaced along the leg. The opposing leg is provided with receptacles that receive and support the closed ends of the protective sleeves. The lead wires are connected to a ballast located in a frame member connecting the two opposing legs.

U.S. Pat. No. 5,902,552 discloses an ultraviolet air sterilization devices that includes a housing and one or more mounts which connect to germicidal lamp units. Each lamp, which projects into the air stream of an air handling duct, has an integral receptacle with an electrical connection for attachment to a ballast from within the housing.

Arrays or assemblies of lamps having electrical terminal pins carried by lamp bases disposed at each end of the lamp tubings is disclosed in a January, 1999 Steril-Aire, USA, Inc. catalog. The ultraviolet lamps are arranged in a fixed dimensional rack whereby the terminal pins located at each end of the ultraviolet lamps are electrically interfaced with receptacles supported by a side frame. The fixed dimensional rack and multiple assemblies of the rack are designed for installation into a HVAC duct system in a variety locations, typically in the air-supply side of the duct system, before and/or after the evaporator coils, or within the mixed air plenum or return air duct.

SUMMARY OF THE INVENTION

In accordance with the present invention, a fluid disinfection module is provided for the treatment of a fluid passing through a conduit. More specifically, an air disinfection module for use in a HVAC duct is provided which comprises a first and second housing arranged in laterally spaced-apart relationship to each other by one or more adjustable support members. Each housing comprises one or more ultraviolet radiation sources, e.g., an ultraviolet light source such as a UV lamp, communicating with and projecting from the housing towards the opposite housing. The ultraviolet radiation sources are generally detachably mounted to each of their housings and communicate with one or more sources of electric power disposed within or without their respective housing. The source of electrical power is typically a ballast for supplying electricity to the ultraviolet radiation source via electric transmission means, e.g., electrical wires connected to a UV lamp.

The ultraviolet radiation source may be an ultraviolet lamp of a straight tubular construction that includes a lamp base disposed at one end thereof for carrying electrical terminal pins mounted thereto. The transmission means includes wiring coupled with a ballast and an electrical receptacle for receiving the terminal pins therein. The ballast may be situated within or without its respective housing, preferably within the housing for including the electronics to operate the ultraviolet lamps. The ultraviolet radiation source may also comprise an ultraviolet lamp having two substantially parallel, tubular sections tubularly connected about one end thereof and terminating in a lamp base that is common to the twin tubular segments. The common lamp base is provided with terminal pins for insertion into an appropriate electrical receptacle that is mounted to the housing. The terminal pins of the lamp are typically engaged with a corresponding electrical receptacle connected to at least one ballast for supplying electricity to the lamp. Each housing of the module generally comprises a plurality of ultraviolet lamps and a plurality of ballasts for supplying electricity to the lamps.

A radiation pervious protective sleeve, typically constructed of fused quartz, is preferably disposed about each ultraviolet radiation source, particularly the ultraviolet lamps having a straight tubular construction used in the fluid disinfection module. The longevity and efficiency of UV lamps used in HVAC systems are generally dependant upon the temperature of the duct air that they are exposed to. The use of a transparent protective sleeve about the radiation sources serves to balance and stabilize the operating temperature of the lamp by insulating the lamp from temperature and humidification fluctuations of the air passing through the HVAC duct. The incorporation of a transparent protective sleeve with the UV lamp allows the lamp to approach optimum performance and increased longevity.

The support members that connect each of the housings for configuring the module may comprise one or more elongate support structures projecting from each housing, the elongate support structure of each housing being slidably engaged with the other for varying the lateral distance between the first and second housings. The elongate support structures are generally disposed about each end of each of the housings, although they may be disposed at one or more locations along the elongate length of the housing. In one aspect of the invention, the elongate support structure for each housing is comprised of a tubular construction such that the tubular support structure of the first housing are slidably engaged and mated with the tubular support structure of the second housing. The tubular support structures of the first and second housings are detachably secured to each other by a locking device, such as, for example, a compression fitting disposed about each respective support structure of the first and second housings. The purpose of using adjustable support structures for connecting the housings to each other is twofold: to provide an adequate framework for supporting the ultraviolet light sources within the module and to enable the distance between the housings to be varied for adapting the lateral width of the module to the corresponding dimensions of a HVAC duct.

In order to add rigidity and structural integrity to the module, particularly when longer length ultraviolet radiation lamps are utilized in, for example, industrial and commercial applications, at least one cross support structure may be mounted to the tubular support structures of the first or second housings. The cross support structure, which may be configured as a fiat, rigid elongate member of metal or plastic construction, is disposed between and substantially parallel to the first and second housings. Appropriate openings are provided in the cross support structure for receiving and supporting the tubular support structures.

In another aspect of the invention, the support structures which connect the first and second housings may be configured as elongate channel members having one end thereof secured about the end of its respective housing. The channels are configured to be slidably engaged with each other. When the proper lateral distance between the housings is reached, the corresponding channels of the first and second housings may be detachably secured to each other by any conventional means, such as but not limited to threaded screws, nut and bolt assemblies, etc.

The cross support structures are also provided with openings for receiving and supporting either the ultraviolet lamps themselves, or radiation pervious protective sleeves with the corresponding ultraviolet lamps contained therein. Securement of the cross support structure to the tubular support structures, protective sleeves and/or ultraviolet lamps may be undertaken by locking devices, for example, compression fittings, grommets or resilient O-rings incorporated into the cross support structure openings and having a resistance fit relative to the tubular support structures, protective sleeves and/or ultraviolet lamps.

Depending on the size of the HVAC duct in question, more than one air disinfection module may be utilized. Accordingly, an array of air disinfection modules described above is contemplated wherein the modules are arranged laterally with respect to each other, preferably with the modules laterally adjacent to each other. The first and second housings of the adjacent modules may be connected to each other or may be common to each other. For example, a first and second module are disposed laterally of each to form an array wherein the second housing of the first module is adjacent to and communicates with the first housing of the second module. Another embodiment is simply to have the second housing of the first module and the first housing of the second module common to each other, i.e., act as one housing.

The array may also include an arrangement whereby the individual modules are stacked. In this embodiment, the first module will overly the second module, in which case, the first housing of the first module may overlie the first housing of the second module, or the first housing of the first module may overlie the second housing of the second module.

The array according to the invention may also comprise more than two modules, with each module being disposed laterally to its adjacent module. As with the dual modules recited above, the first and second housings of the adjacent modules may be connected to each other or combined to function as one common housing.

BRIEF DESCRIPTION OF THE DRAWINGS

A complete understanding of the present invention may be obtained by reference to the following specification when taken in conjunction with the accompanying drawings wherein certain preferred embodiments are illustrated and wherein like numerals refer to like parts throughout.

FIG. 13 is an exploded isometric view of detail F illustrated in FIG. 12.

FIG. 14 is an isometric view of another embodiment of the fluid disinfection module illustrated in FIG. 13.

DETAILED DESCRIPTION OF THE INVENTION AND PREFERRED EMBODIMENTS THEREOF

Throughout the following description, the preferred embodiments and examples are intended as exemplars rather than limitations on the apparatus of the present invention.

The present invention provides an apparatus for the germicidal treatment of a fluid, and more specifically to an apparatus that disinfects air passing through a HVAC duct utilizing one or more radiation sources. The apparatus described herein has the advantage of being adaptable to HVAC ducts of various cross-sectional dimensions such as those found in commercial and industrial buildings that employ large heating/air conditioning equipment for moving high magnitudes of air. The apparatus typically takes the form of a module that employs at least one, generally a plurality, of ultraviolet lamps whose disposition within the HVAC duct is configured for maximum exposure to the passage of air therethrough.

Figure 1:
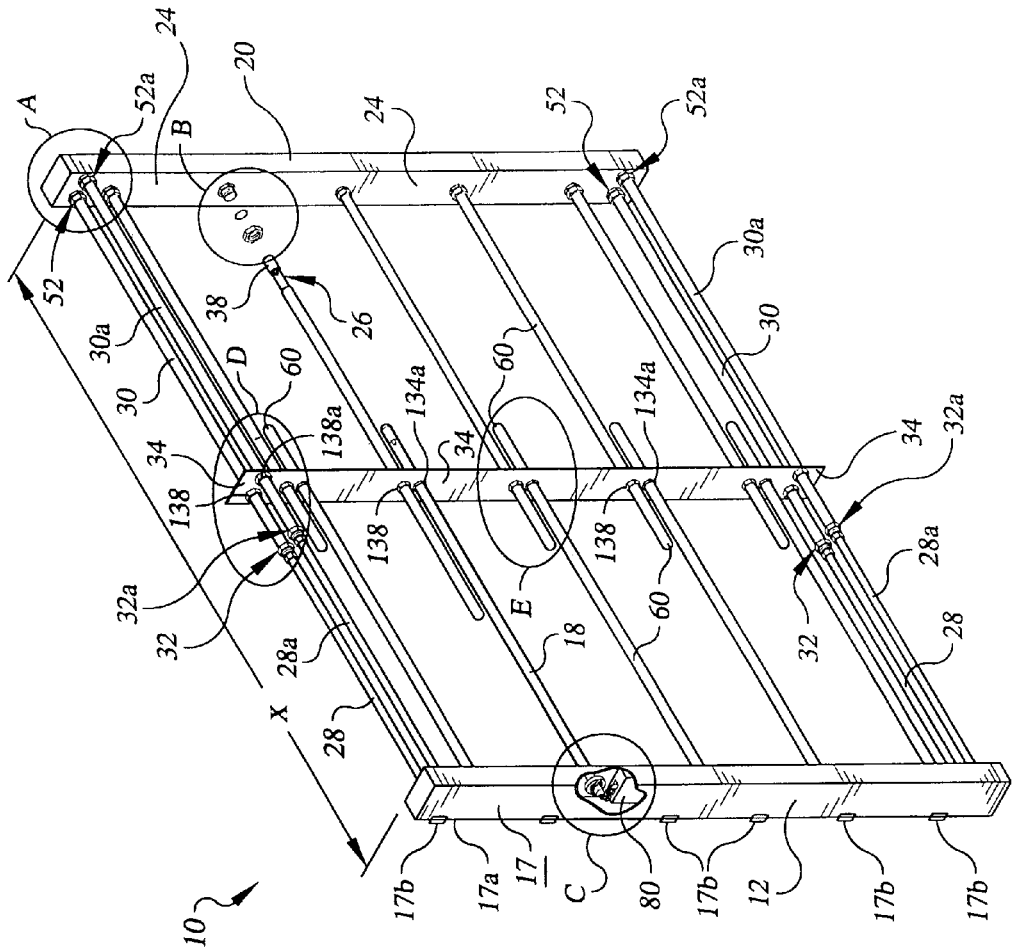
FIG. 1 is an isometric view of a fluid disinfection module in accordance with one embodiment of the invention.
Figure 2:
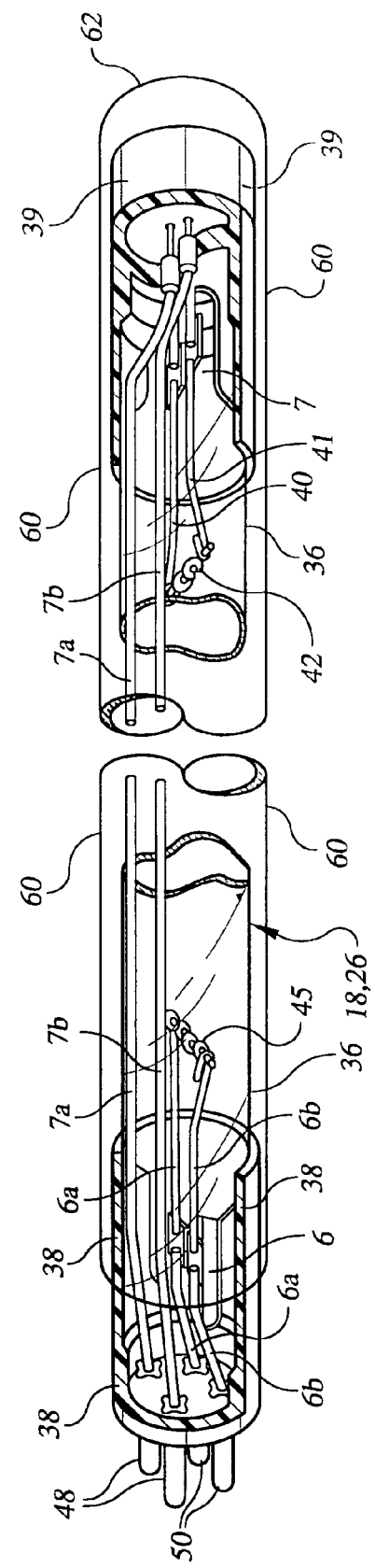
FIG. 2 is an elevated cross-sectional plan view of the quartz sleeve illustrated in FIG. 1 surrounding an ultraviolet lamp in accordance with an embodiment of the invention herein.

Referring to the drawings, specifically FIG. 1, there is shown for illustrative purposes only, an fluid disinfection module 10 constituting one embodiment of the invention herein. Module 10 is structured for adaptation to HVAC ducts of varying dimensions for the disinfection of air, and has a framework-type configuration comprising a first elongate housing 12 having a generally rectangular cross-section. As better shown in FIG. 3, housing 12 is provided with at least one opening 14 on one elongate side 16 thereof, preferably a plurality of such openings, for receiving therein for mounting with housing 12 a corresponding number of ultraviolet radiation sources in the form of elongate tubular ultraviolet ("UV") lamps 18, whose details are illustrated in FIG. 2. Referring to FIG. 4, module 10 also comprises a second elongate housing 20 similar to housing 12 in that it also has a generally rectangular cross-section provided with at least one opening 22 on one elongate side 24 thereof, preferably a plurality of openings. A corresponding number of ultraviolet radiation sources in the form of tubular UV lamps 26 are received in the respective openings 22 for mounting with housing 20. In forming the framework-like configuration of module 10 (see FIG. 1), housing 12 is provided with a pair of tubular support members 28, 28a having a circular cross-section, one end of each member being secured to elongate side 16 by means of compression fittings 52,52a, respectively, the detail of which is partially illustrated in FIG. 5. Tubular support members 28,28a are arranged to laterally project from side 16 (shown in FIG. 3) in a substantially perpendicular direction towards housing 20.

Figure 1A:
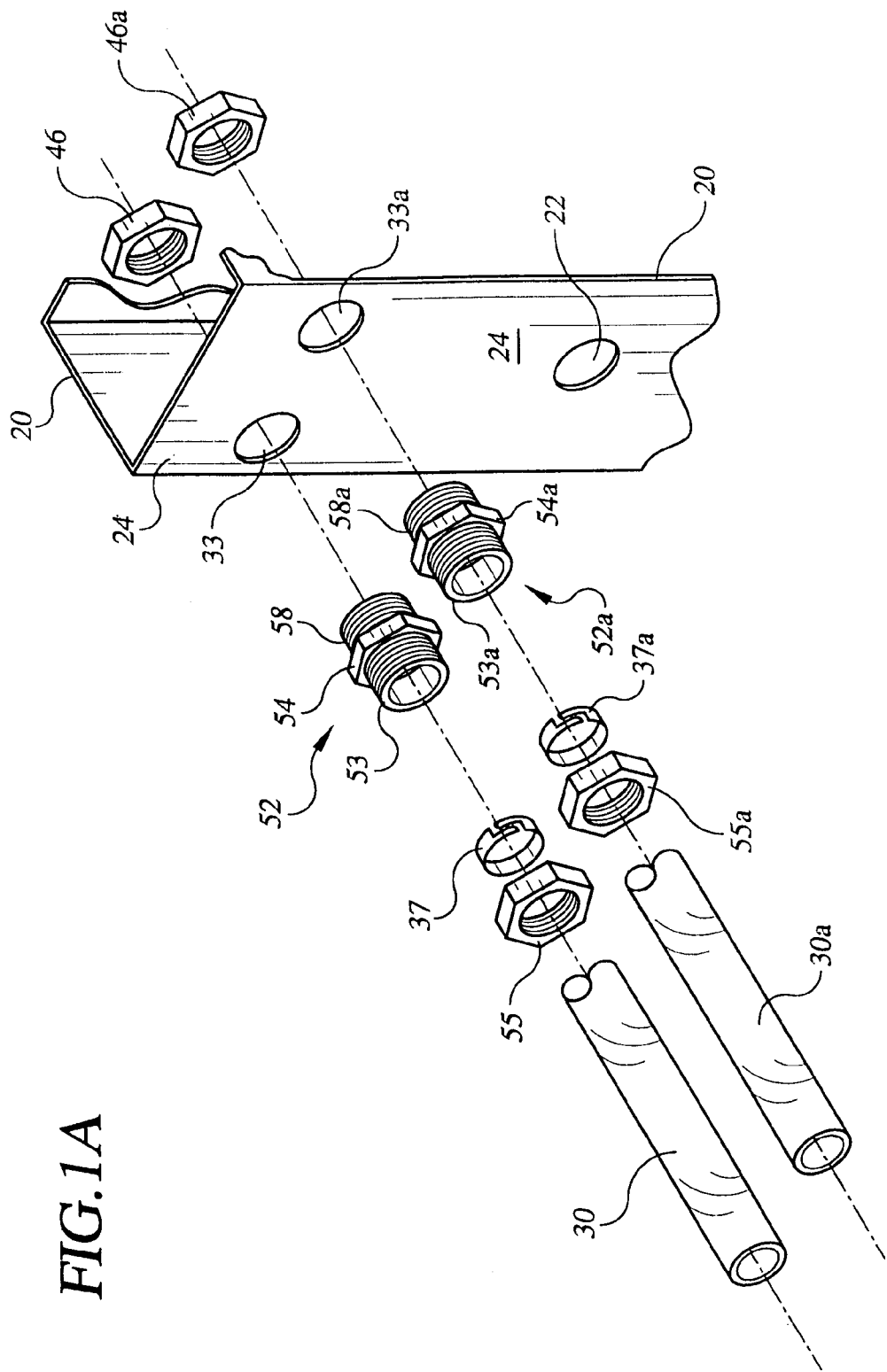
FIG. 1A is an exploded fragmentary isometric view of detail A illustrated in FIG. 1.
Figure 5A:
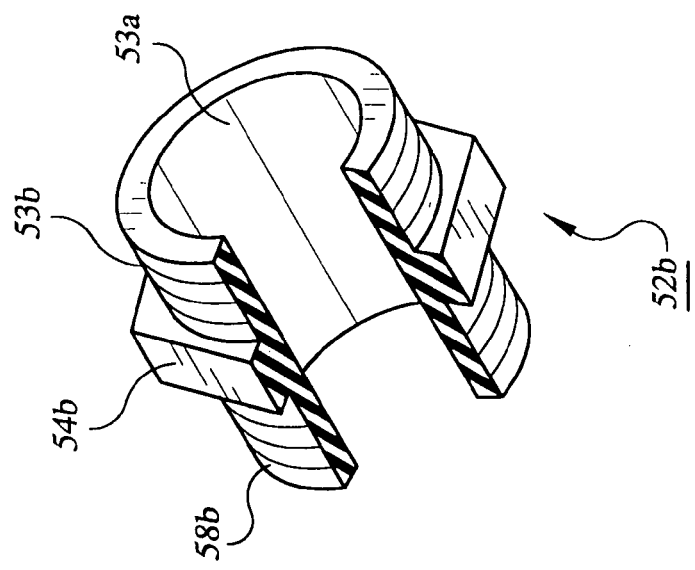
FIG. 5A is an enlarged segmented isometric view of compression fitting 52b illustrated in FIG. 3.
Figure 5:
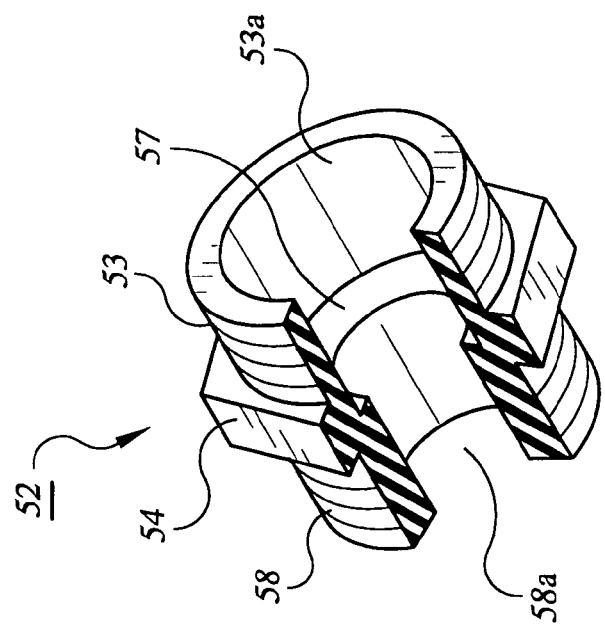
FIG. 5 is an enlarged segmented isometric view of compression fitting 52 illustrated in FIG. 4.

In similar fashion, a second elongate housing 20 is provided with a pair of tubular support members 30,30a, one end of each being secured to elongate side 24 of housing 20 in the manner illustrated in FIG. 1A. FIG. 1A enlarges on the area defined by Detail A shown in FIG. 1. While other configurations may be employed, the manner of the joinder of tubular support members 28,28a to housing 12 is identical to the joinder of tubular support members 30,30a to housing 20, i.e., by the use of compression fittings 52,52a. Referring to FIGS. 1A and 5, compression fittings 52,52a have exteriorly threaded annular extensions 53,53a and 58,58a projecting from either side of a hexagonal-shaped nut 54,54a, respectively. Annular extensions 58,58a are configured for slidable insertion through openings 33,33a provided in elongate side 24. Once hexagonal-shaped nuts 54,54a interface with the exterior surface of elongate side 24, locking nuts 46,46a positioned on the interior side of elongate side 24 are engaged with annular extensions 58,58a for the securement of compression fittings 52,52a to housing 20. Hexagonal-shaped nuts 54,54a and locking nuts 46,46a therefore function as flanges for the containment of elongate side 24 therebetween. As shown in greater detail in FIG. 5, annular extension 58 (as well as extension 58a) is sized to be smaller in diameter than annular extension 53 (and 53a), which results in the provision of an annular seat 57 located within the confines of compression fittings 52,52a. Therefore, when the ends of tubular support members 30,30a are inserted through compression nuts 55,55a and annular split rings 37,37a into compression fittings 52,52a, respectively, they will come to rest against annular seat(s) 57, the annular seat 57 being axially located in FIG. 5 within the confines of hexagonal-shaped nut 54. Annular split rings 37,37a, formed from a metal or plastic construction, are respectively sized to fit within compression nuts 55,55a which are configured for threaded engagement with annular extensions 53,5a. The engagement of compression nuts 55,55a with compression fittings 52,52a will cause split rings 37,37a to be compressed about the ends of tubular support members 30,30a, respectively, thereby securing the tubular support members to housing 20. In this manner, tubular support members 30,30a are enabled to laterally project from side 24 in a substantially perpendicular manner towards housing 12. The utilization of properly sized compression fittings 52,52a with tubular support members 28,28a also enables securement of those tubular support members to housing 12 in the same manner.

While other locations along the length of elongate sides 16 and 24 are possible, tubular support members 28,28a and 30,30a are positioned about and secured to the ends of their respective housings with compression fittings 52,52a such that they are in axial alignment with respect to each other. Each of the tubular support member pairs are sized in diameter for slidable insertion within the other. This arrangement allows the lateral distance x between housings 12 and 20 to be varied for enabling the placement and securement of module 10 within the HVAC duct. Either pair of tubular support members 28,28a and 30,30a may have the smaller diameter and thereby serve as the male segment in their mateable relationship with each other. Alternatively, tubular support members 28 and 30a may have the smaller diameter and serve as the male components of the mateable relationship. Tubular support members 28,28a and 30,30a are maintained in fixed relationship with each other by the employment of a locking device 32 as identified by the circled Detail D in FIG. 1, and the details of which are described below and illustrated in FIGS. 7 and 8.

Equipped with the foregoing framework-like structure, the lateral distance x of module 10 can be varied to adapt to the corresponding dimension of a HVAC duct. Accordingly, depending on the internal dimensions of the HVAC duct for which the module is intended, UV lamps 18 and 26 can vary in length. For example, UV lamps 18 and 26, which include a lamp base 38 that supports electrical terminal pins 48,50 at one end of the lamp (see FIG. 2) for engagement with an appropriate socket retained by housings 12 and 20, are generally manufactured in variety of lengths by different manufacturers. Typical approximate lengths are 12 inches, 16 inches, 24 inches, 30 inches, 36 inches, 48 inches, and 61 inches, although any length can be ordered. For most industrial and commercial applications which employ large HVAC duct systems, the longer length UV lamps will be utilized, e.g., lengths of 33¼ (referred to as G-36 lamps) and 61³⁄₁₆ inches (referred to as G-64 lamps). When longer length UV lamps are utilized (such as the UV lamps 18 and 26 illustrated in FIG. 1.), it may become necessary to add structural support and rigidity to the framework-like module 10, and a cross support member may optionally be included with the module. As shown in FIG. 1, a cross support member 34 is included and configured to be mounted to tubular support members 30,30a and the quartz sleeves surrounding UV lamps 18 and 26. The implementation of cross support member 34 with tubular support members 30,30a is specifically identified by Detail D in FIG. 1, which is illustrated in greater detail in FIGS. 7-8. Detail E in FIG. 1 identifies the coupling of cross support member 34 with UV lamps 18 and 26 and is expanded upon in FIG. 11. And in Detail B in FIG. 1, which is expanded upon in FIGS. 2 and 4, UV lamps 18 and 26 may optionally be encased with quartz sleeves 60 to balance the operating temperature of the lamp and prevent it from being subjected to extreme temperatures that the air passing through an HVAC duct may exhibit.

As illustrated in FIG. 1, each of UV lamps 18 and 26 projects from their respective housings 12 and 20 along a longitudinal axis that is substantially perpendicular to the opposing housing. The axes of UV lamps 18 are offset relative to the axes of UV lamps 26 in order to avoid contact of the lamps with each other when UV lamps 18 and 26 overlap. UV lamps 18 and 26 will always have a slight to moderate overlap in order to avoid the creation of a zone within which the air passing through the HVAC duct will not be fully exposed to the effects of radiation emanating from the UV lamps. Detail B of FIG. 1 illustrates the manner of attachment of the UV lamps with their respective housings which is expanded upon in FIGS. 2-4.

FIG. 2 illustrates UV lamps 18 and 26 in greater detail. UV lamps 18 and 26 are conventional, low pressure, ultraviolet lamps whose multiple electrical terminal pins are contained at one end thereof for electrical connection with a power supply preferably contained within housings 12 and 20, respectively. In the embodiment illustrated in FIGS. 2-4, a two pairs of electrical terminal pins 48 and 50 are secured to and emanate from lamp base 38. The UV lamp of FIG. 2 comprises a vacuumed, quartz tubular portion 36, i.e., a "hard glass" lamp, that is sealed at the collapsed ends 6 and 7 thereof. It will be noted that in place of a "hard glass" lamp, a two- or four-pin "soft glass" UV lamp manufactured by the Phillips Corporation may be used which has a tubing that is permeable to ultraviolet light in the wavelength range that includes 254 nanometers. Each end of tubular portion 36 is respectively retained and supported by lamp bases 38 and 39 which may be formed from a suitable ceramic or plastic material, preferably molded plastic. Ends 6 and 7 contain respective electrode filaments 45 and 42. Lamp base 39 houses the ends of a pair of wires 40,41 emanating filament 42 through the sealed end 7 of tubular portion 36. A pair of lead wires 7a,7b connects respectively with wires 40,41 and extend along the outside of tubular portion 36 for connection with a pair of electrical pins 48 axially extending from lamp base 38. Filament 45 at the opposite end of tubular portion 36 is electrically coupled with conductor wires 6a,6b extending through collapsed end 6 which in turn are connected to the remaining pair of terminal pins 50 also axially extending from lamp base 38. When filaments 45,42 are supplied with electrical power, they serve to energize and vaporize mercury contained within vacuumed tubular portion 36. UV lamp 26 illustrated in FIGS. 1, 3-4, 10, and 15-16 have an identical construction for mounting with its respective housing 20, and like UV lamp 18, may be a "hard glass" or "soft glass" lamp. UV lamps 18 and 26 can optionally be provided with a protective quartz sleeve 60 whose purpose and function is described in greater detail below.

Figure 3:
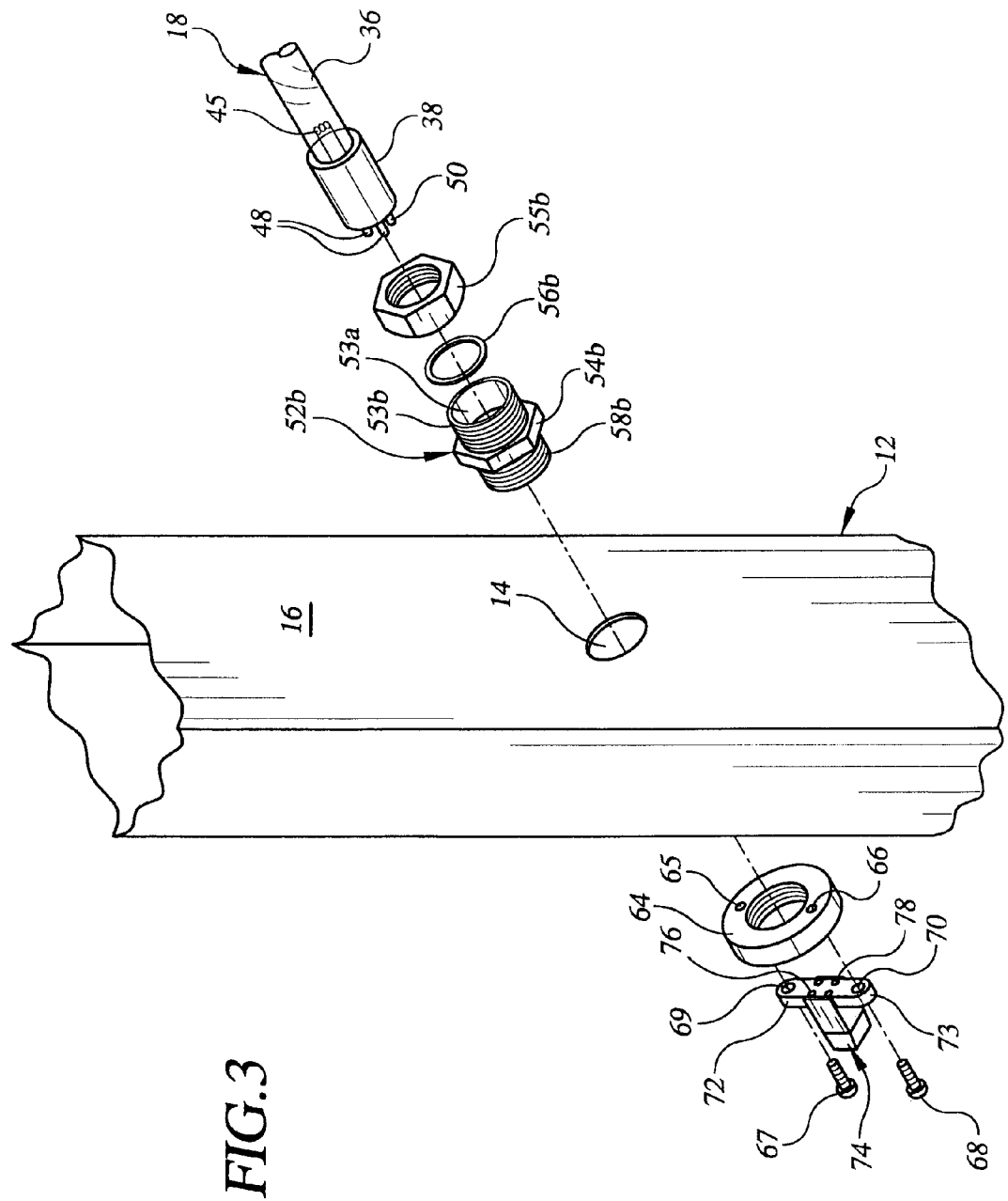
FIG. 3 is an exploded isometric view of detail B illustrated in FIG. 1.
Figure 4:
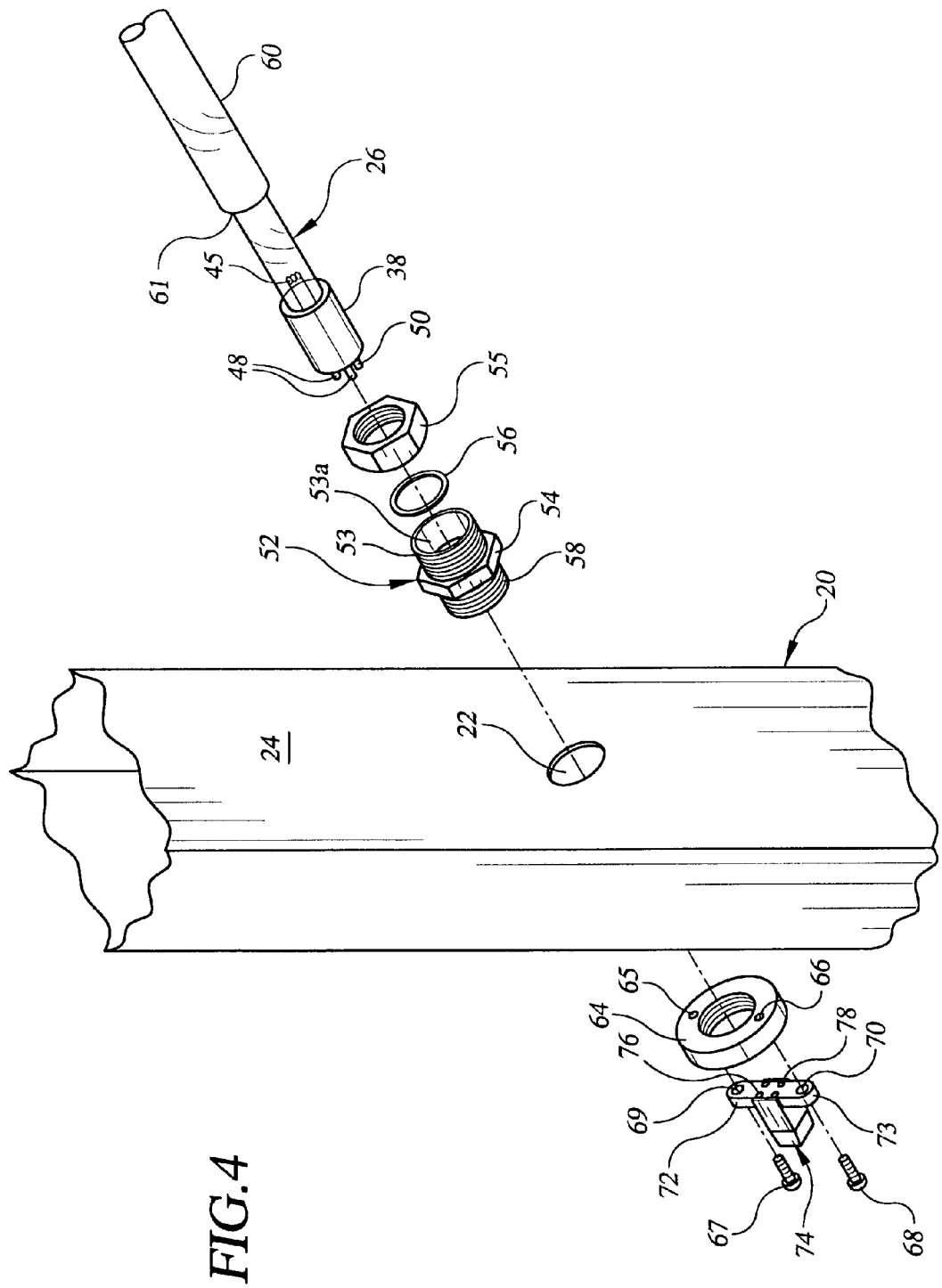
FIG. 4 is an exploded isometric view of another embodiment for detail B illustrated in FIG. 1.

UV lamps 18 and 26 may be secured to their respective housings 12 and 20 in any number of ways, an example of which is illustrated in FIG. 3. Referring to FIGS. 3 and 5A, a threaded compression fitting 52b has exteriorly threaded annular extensions 53b and 58b projecting from either side of and integral with a hexagonal-shaped nut 54b. As detailed in FIG. 5A, annular extension 58b is configured to be of the same diameter as extension 53b thereby providing a common annular opening 53a. Referring once again to FIG. 3, the diameter of annular extension 58b is sized to slidably extend through opening 14 of housing 12, and once inserted therein, the mounting of compression fitting 52b to elongate side 16 is undertaken by the threaded engagement of annular coupling member 64 with extension 58b. Annular coupling member 64 is configured in size to be greater than opening 14 and may take any shape or form to act as a flange for contact with the interior surface of elongate side 24. The coupling member may be manufactured from, for example, a hardened plastic material such as polyvinylchloride, although any metal construction of brass, steel, stainless steel, aluminum, cast zinc, etc. may be utilized. Hexagonal-shaped nut 54b and coupling member 64 therefore embrace elongate side 16 therebetween to fix compression fitting 52b to housing 12.

As shown in FIG. 3, annular coupling member 64 is provided with two threaded openings 65,66, for receiving a pair of fasteners, e.g., correspondingly threaded bolts 67,68, respectively, that are designed to pass through a pair of openings 69,70 contained within wing extensions 72,73 of electrical socket 74 (see FIG. 6) to secure the socket to coupling member 64. Electrical socket 74 connects with electrical terminal pins 48,50 by receiving them into electrical receptacles 76,78. As already noted above, annular coupling member 64 is configured in size to be substantially larger than opening 14 to act as a flange against the interior of elongate side 24, and in addition to provide a suitable support for wing extensions 72,73 of socket 74.

Once compression fitting 52b is secured to housing 12 along with the coupling of electrical socket 70 to coupling member 64, the mounting of UV lamp 18 follows. An annular O-ring 56b is provided and sized to fit within an internally threaded compression nut 55b. Compression nut 55b is configured for threaded engagement with annular extension 53b. The annular openings of the O-ring and compression nut are configured for slidably receiving lamp base 38 therethrough. Lamp base 38 of UV lamp 18 is then inserted through compression nut 55b, O-ring 56b, and into opening 53a of compression fitting 52b. Once inserted, the terminal pins 48,50 of lamp base 38 are engaged with their corresponding female electrical receptacles 76,78. The engagement of compression nut 55b with annular extension 53b will then cause O-ring 56b to be compressed about lamp base 38 for the securement of UV lamp 18 to compression fitting 52b and to housing 12. In this fashion, UV lamp 18 is enabled to laterally project from its respective housing 12 towards its opposite housing 20. UV lamp 26 may be secured to housing 20 in the same fashion.

As noted herein, and as best illustrated in FIGS. 2 and 4, each of UV lamps 18 and 26 may optionally be provided with a transparent protective sleeve, typically a quartz sleeve 60 that is pervious to the ultraviolet light emitted by UV lamps 18 and 26, or a sleeve constructed of ultraviolet light pervious materials such as Kynar® or Teflon®. Encasing the UV lamps with a transparent protective sleeve has several advantages. HVAC duct systems generally function by admitting air from an outside environment and then subjecting it to filtration, cooling and/or heating, and/or humidification, and finally transporting it through the HVAC duct system to a plurality of domestic rooms or commercial and industrial spaces, and even vehicles such as automobiles and public transport vehicles, e.g., airplanes, buses, trains, etc. Temperature variations of the air passing through a HVAC duct, depending on the air's treatment, are therefore inevitable and become one of the factors that determine the longevity and efficiency of a radiation lamp used for air disinfection. For example, as cooler duct air temperatures lower the skin temperature of the lamp's tubing, the operating temperature of the mercury vapor contained within the lamp's tubing will tend to drop. If the operating temperature is sufficiently lowered, the mercury vapor pressure will also be lowered and less ultraviolet radiation will be produced. Therefore, when heat is drawn away from the lamp by the cooler HVAC duct air, the ultraviolet light output of the lamp will decrease. As shown in FIGS. 1 and 4, the utilization of UV lamps 18 and 26 that are encased with quartz sleeves 60 serves to balance the operating temperature of the UV lamps and prevent them from being subjected to extreme temperatures of the air passing through an HVAC duct in which module 10 is disposed. Optimum performance of the lamps, accompanied by an increased longevity, is therefore provided.

As best shown in FIG. 2, quartz sleeve 60 has an open end 61 for receiving UV lamp 18 (as well as UV lamp 26) therein, and is closed at its opposite end with a dome-shaped end 62. The open end 61 is sized to slidably fit about the circumference of lamp bases 39 and 38. In addition, the length of quartz sleeve 60 is configured to allow the end of lamp base 39 to butt against the dome-shaped end 62 of quartz sleeve 60 with the open end 61 terminating at approximately the midpoint of lamp base 38. The foregoing will have the effect of concentrically centering the tubular portion 36 of UV lamp 18 within quartz sleeve 60 to avoid its contact with the sleeve's inside surface. UV lamps 18 and 26 may be fixed within their respective quartz sleeves 60 by the application of an appropriate fixative and sealant between the inside surface of the open end 61 of sleeve 60 and the outside surface of UV lamp base 38. An example of a fixative and sealant is an ultraviolet light curative epoxy cement available from Norland Products Inc. under the name of Norland Electronic Adhesive.

The mounting of the UV lamp and protective sleeve assemblies to their respective housings is accomplished in much the same way as the mounting of UV lamp 18 to housing 12 illustrated in FIG. 3. The exception is that a compression fitting of the type illustrated in FIG. 5 is used. Referring to FIG. 5, compression fitting 52, like compression fitting 52b, includes two annular extensions 53,58 axially extending from hexagonal-shaped nut 54. The annular opening 58a of extension 58 is smaller in diameter than the annular opening 53a of extension 53. Extension 58 terminates approximately internally of hexagonal nut 54 to provide an annular seat 57. Annular extensions 53,58 and hexagonal-shaped nut 54 combine to form an integrated compression fitting constructed of, for example, a metal material such as brass, steel, stainless steel, cast zinc, aluminum, etc. The annular opening 58a of extension 58 is sized to receive lamp base 38 therethrough, but not quartz sleeve 60. Only the opening 53a of annular extension 53, compression nut 55, and O-ring 54 is sized to receive the larger diameter quartz sleeve 60 therein. The annular seat 57 acts as a stop for the open end 61 of quartz sleeve 60 when the sleeve is mounted over UV lamp 26 and inserted into compression fitting 52.

FIG. 4 expands upon Detail B shown in FIG. 1 and illustrates the mounting of UV lamp 26 and its quartz sleeve 60 to housing 24. As with compression fitting 52b, the mounting of compression fitting 52 to housing 20 (see FIG. 4) is undertaken by inserting annular extension 58 through opening 22 of elongate side 24 and securing it to side 24 by the threaded engagement of interiorly threaded annular coupling member 64. The coupling of electrical socket 70 with coupling member 64 is the same as that described for the mounting of UV lamp 18 to housing 12 illustrated in FIG. 3. Once compression fitting 52 is secured to housing 20 along with the coupling of electrical socket 70 to coupling member 64, lamp base 38 containing quartz sleeve 60 mounted thereto (in the manner illustrated in FIG. 2) is inserted through compression nut 55, O-ring 56, and into the annular opening 53a of extension 53. The length of quartz sleeve 60 is such that lamp base 39 of UV lamp 26 (see FIG. 2) will interface against the dome-shaped end 62 of the sleeve. Once the lamp and its quartz sleeve are positioned in compression fitting 52, and its electrical terminal pins 48,50 subsequently connected to electrical socket 70, the engagement of compression nut 55 with annular extension 53 causes O-ring 56 to be compressed about quartz sleeve 60 for the securement of the lamp and sleeve to compression fitting 52 and to housing 20. As a result, UV lamp 26 and its protective quartz sleeve 60 are enabled to laterally project from their respective housing 20 towards its opposite housing 12. It will be understood that both UV lamps 18 and 26 may utilize protective sleeves as is illustrated in FIG. 1.

Figure 7:
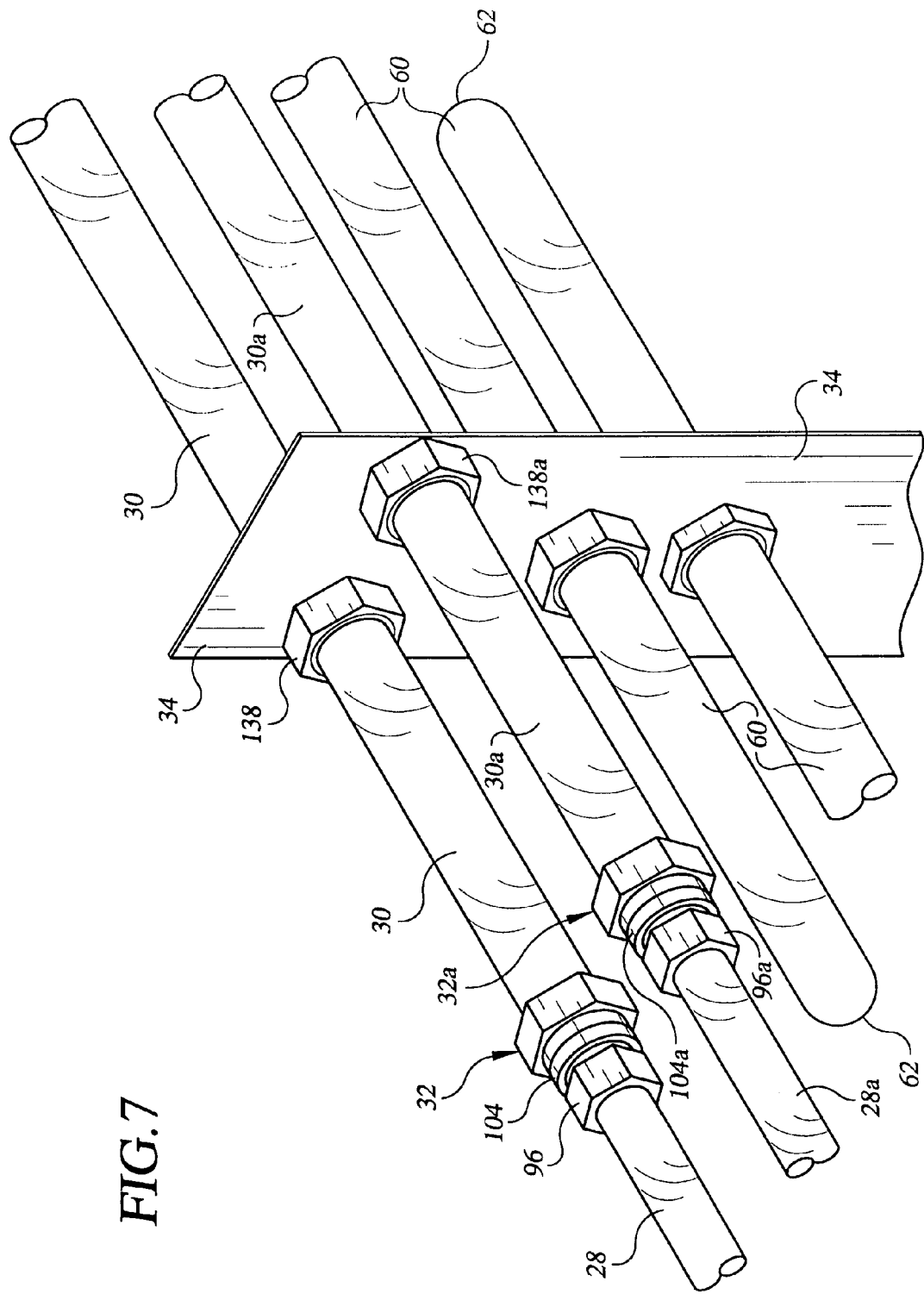
FIG. 7 is an enlarged isometric view of detail D illustrated in FIG. 1.
Figure 8:
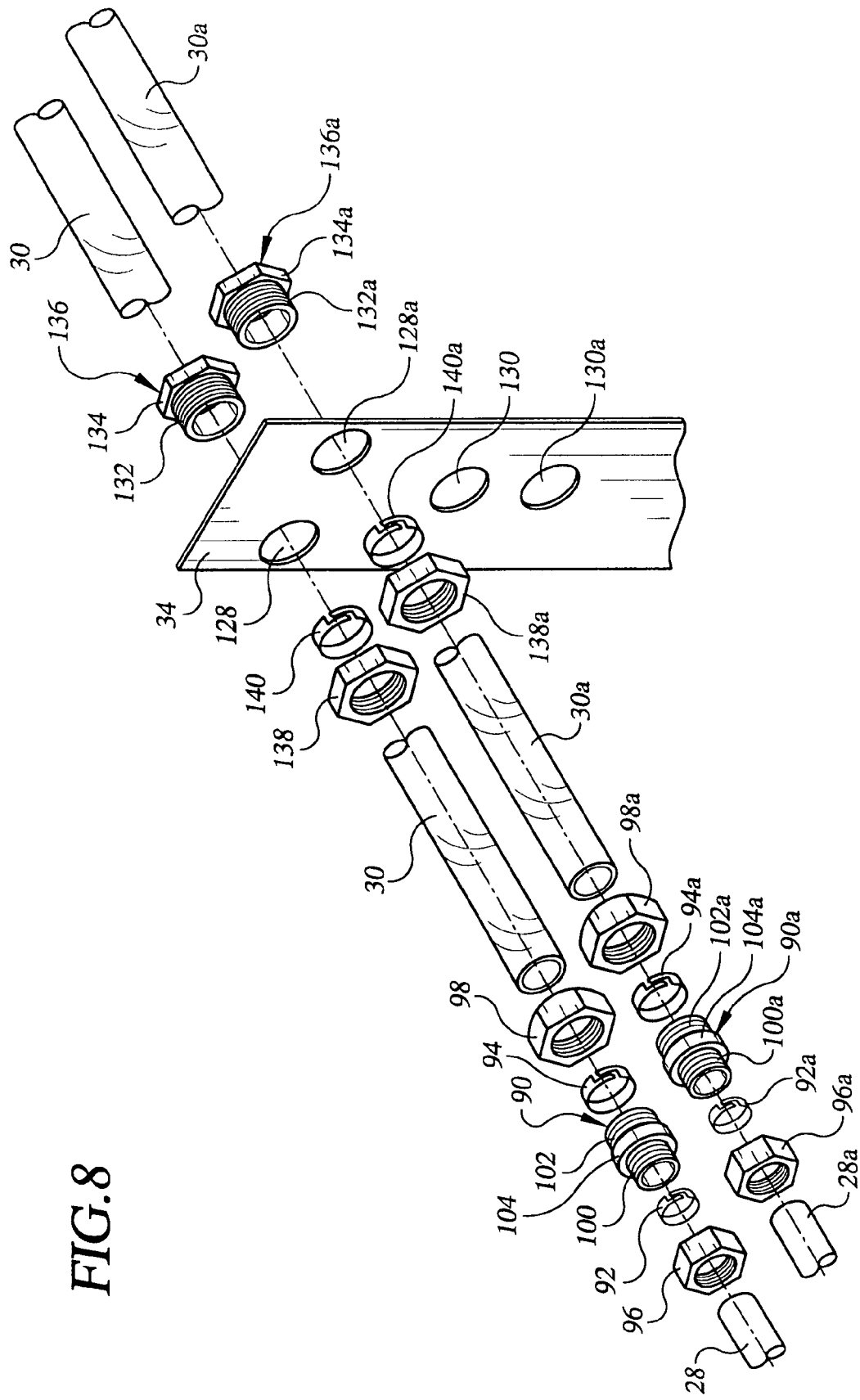
FIG. 8 is an exploded isometric view of detail D illustrated in FIG. 1.

As described hereinbefore and illustrated in FIGS. 1 and 7, housings 12 and 20 are formulated into a framework configuration by means of the slidable engagement of tubular support members 28,28a and 30,30a with each other which are held in place by locking devices 32,32a, respectively. Referring to FIGS. 7 and 8, locking devices 32,32a comprise compression fitting adapters 90,90a, compression rings 92,92a and 94,94a, and compression nuts 96,96a and 98,98a, respectively. Each of compression fitting adapters 90,90a, which is an integral fitting that can be formed from a plastic or metal material, e.g., polyvinylchloride, brass, galvanized steel, stainless steel, aluminum, etc., has exteriorly threaded annular extensions 100,100a and 102,102a extending in opposite directions from common members 104,104a, respectively. Annular extensions 100,100a necessarily have a smaller annular opening relative to annular extensions 102,102a for slidably receiving therethrough tubular support members 28,28a. Annular extensions 102,102a, on the other hand, have a larger opening for receiving tubular support members 30,30a therein the ends of which will come to rest against an annular stop (not shown, but similar to annular seat 57 of compression fitting 52 illustrated in FIG. 5) created by the respective termination of annular extensions 100,100a at or within the confines of common members 104,104a. Each of annular extensions 100,100a and 102,102a are respectively provided with correspondingly threaded compression nuts 96,96a and 98,98a which are respectively configured for slidable engagement with their corresponding tubular support members 28,28a and 30,30a. Together with concentric split rings 92,92a and 94,94a, corresponding compression nuts 96,96a and 98,98a will clamp the split rings about the exterior surface of their tubular support members 28,28a and 30,30a when the compression nuts are threaded onto their respective annular extensions for locking the tubular support members in place. With this arrangement, the lateral distance x between housings 12 and 20 (see FIG. 1) can be adjusted to the corresponding inner lateral dimensions of a HVAC duct by sliding tubular support members 28,28a within tubular support members 30,30a and locking them in place with locking devices 32,32a.

Figure 9:
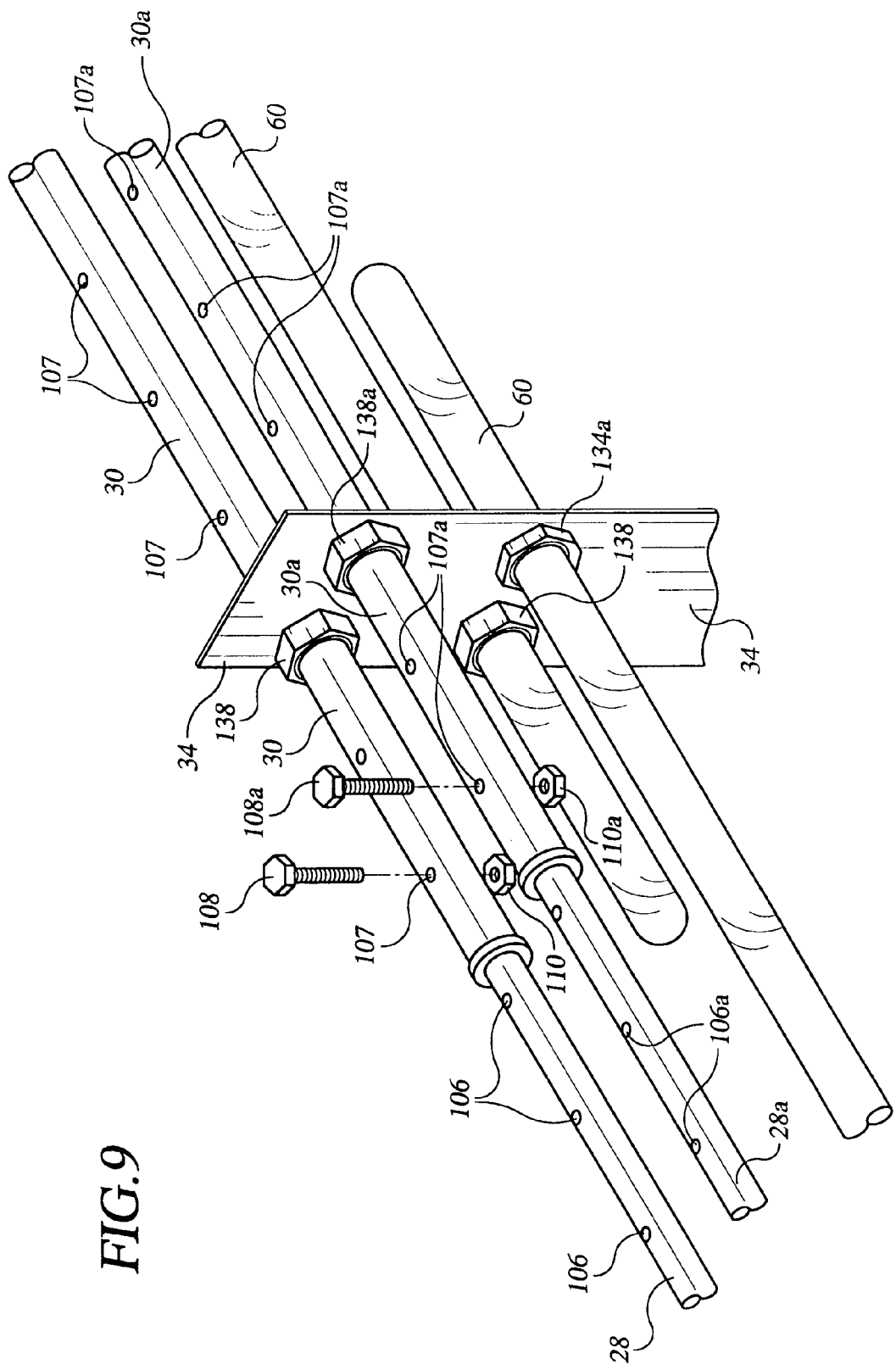
FIG. 9 is an isometric view of another embodiment of the invention illustrated in FIG. 7.

An alternative locking device for maintaining tubular support members 28,28a and 30,30a in place is illustrated in FIG. 9. In this embodiment, each of tubular support members 28,28a and 30,30a is provided with a series of openings 106,106a and 107,107a, respectively, on opposite sides of and along the length thereof for receiving therethrough threaded bolts 108,108a for engagement with correspondingly threaded nuts 110,110a. This has the effect of securing the respective tubular support members 28,28a and 30,30a to each other. Openings 106,106a and 107,107a are incrementally spaced apart along each of their respective tubular support members 28,28a and 30,30a such that openings 106, 106a will be in alignment with openings 107,107a when the insertion of tubular support members 28,28a into tubular support members 30,30a is varied by a predetermined distance. The predetermined distance is established by the spacing of openings 107,107a along the length of tubular support members 30,30a identically with the spacing of openings 106,106a along tubular support members 28,28a. This facilitates the insertion of threaded bolts 108,108a into openings 106,106a and 107,107a.

Figure 10:
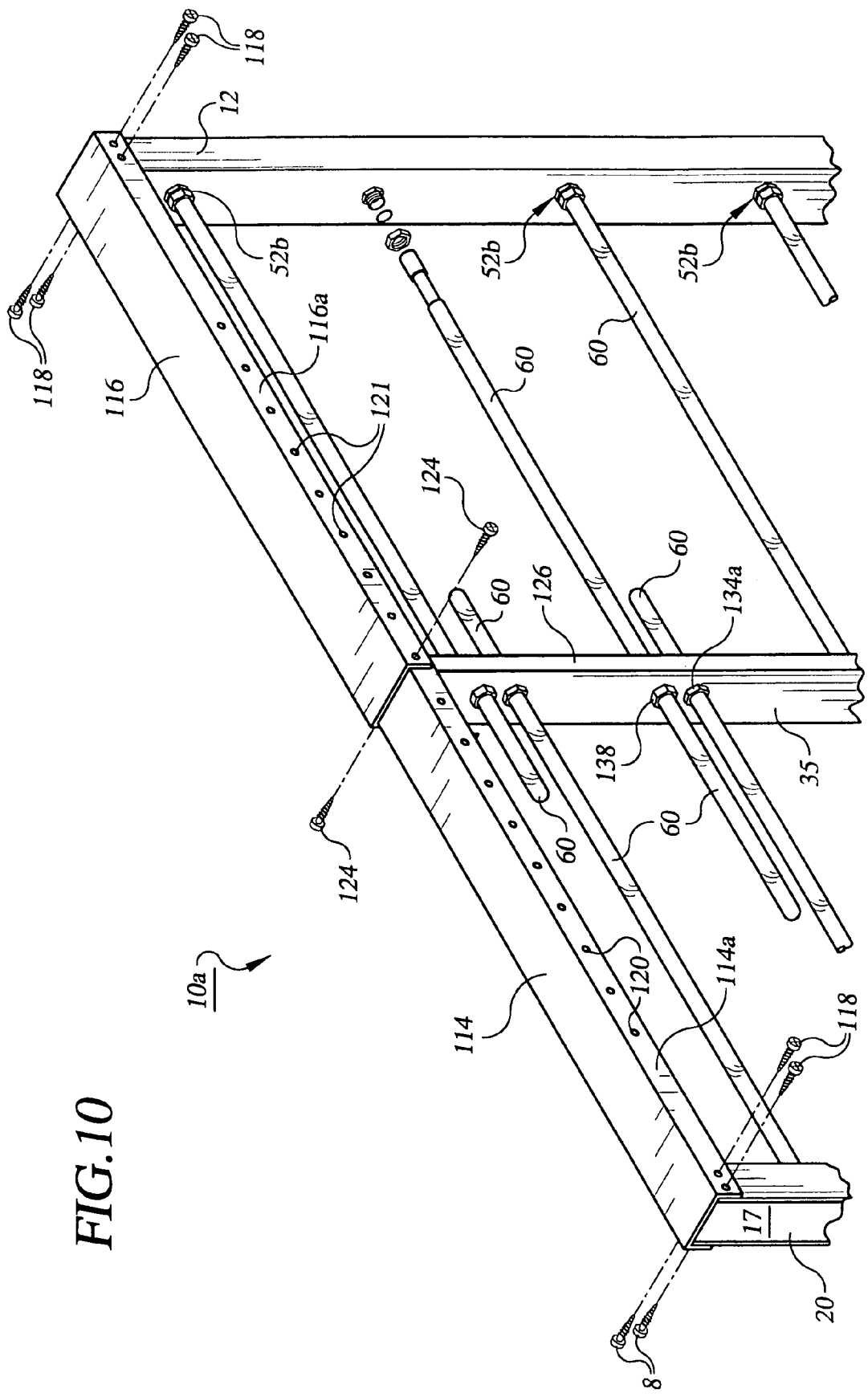
FIG. 10 is a partial isometric view of yet another embodiment of the invention illustrated in FIG. 1.

Another embodiment for varying the lateral distance x between housings 12 and 20 is illustrated in FIG. 10 wherein in place of tubular support members 28,28a and 30,30a, or in conjunction therewith, channel support members 114 and 116, disposed at both ends of housings 12 and 20, are used as the first and second housing support structures, respectively, for establishing a framework-like module 10a. Accordingly, the width of the channel of channel support member 114 is configured in size for placement over and for encompassing the end of housing 12 as shown in FIG. 10. In like manner, one end of channel support member 116 is placed over and encompasses the end of housing 12. The respective ends of channel support members 114 and 116 may be fastened to their housing ends by any conventional means, for example, by the use of threaded sheet metal screws, bolts, or the like, inserted through the sides of the channel members into elongate sides 14 and 24 of housings 12 and 20, respectively. Sheet metal screws 118 are illustrated in FIG. 10.

Channel support members 114 and 116 are configured in size such that one will be slidably received within the channel of the other. As shown in FIG. 10, channel support member 114 is slidably disposed within channel support member 116. As with tubular support members 28,28a and 30,30a, the respective side walls 114a and 116a of channel support members 114 and 116 are provided with a plurality of spaced-apart openings 120,121, respectively, along the length thereof for receiving threaded bolts 124 when the openings 120,121 are in alignment with each other. In order to adjust the lateral distance between housings 12 and 20, channel support members 114 on both ends of housing 20 are slid into the corresponding channel support members 116 of housing 12 to a desired depth. Once openings 120,121 are aligned, channel support members 114 and 116 are fastened to each other by the insertion of threaded bolts 124, preferably in more than one openings 120,121 along the length of channel support member 116 to add rigidity to the combined channel support members 114,116.

It will be understood that any number and variety of mechanisms may be used to detachably secure the first and second housing support structures to each other, including, for example, a locking device that utilizes an annular compression fitting such as that identified by reference numerals 32 or 32a illustrated in FIG. 7 when the support structures are of a tubular construction, or a threaded screw or nut-and-bolt assembly when slidably engaged channels are used as illustrated in FIG. 9. It will also be appreciated that tubular support members 28,28a and 30,30a, as well as channel support members 114 and 116, may be secured to each other in other ways. For example, once the mating of the respective support members is undertaken and the lateral distance x between housings 12 and 20 is fixed, they can be fixed to each other by simply drilling one or more holes through the members, and inserting through the hole(s) an appropriate locking device, such as a nut and bolt combination, locking pin, etc.

Figure 11:
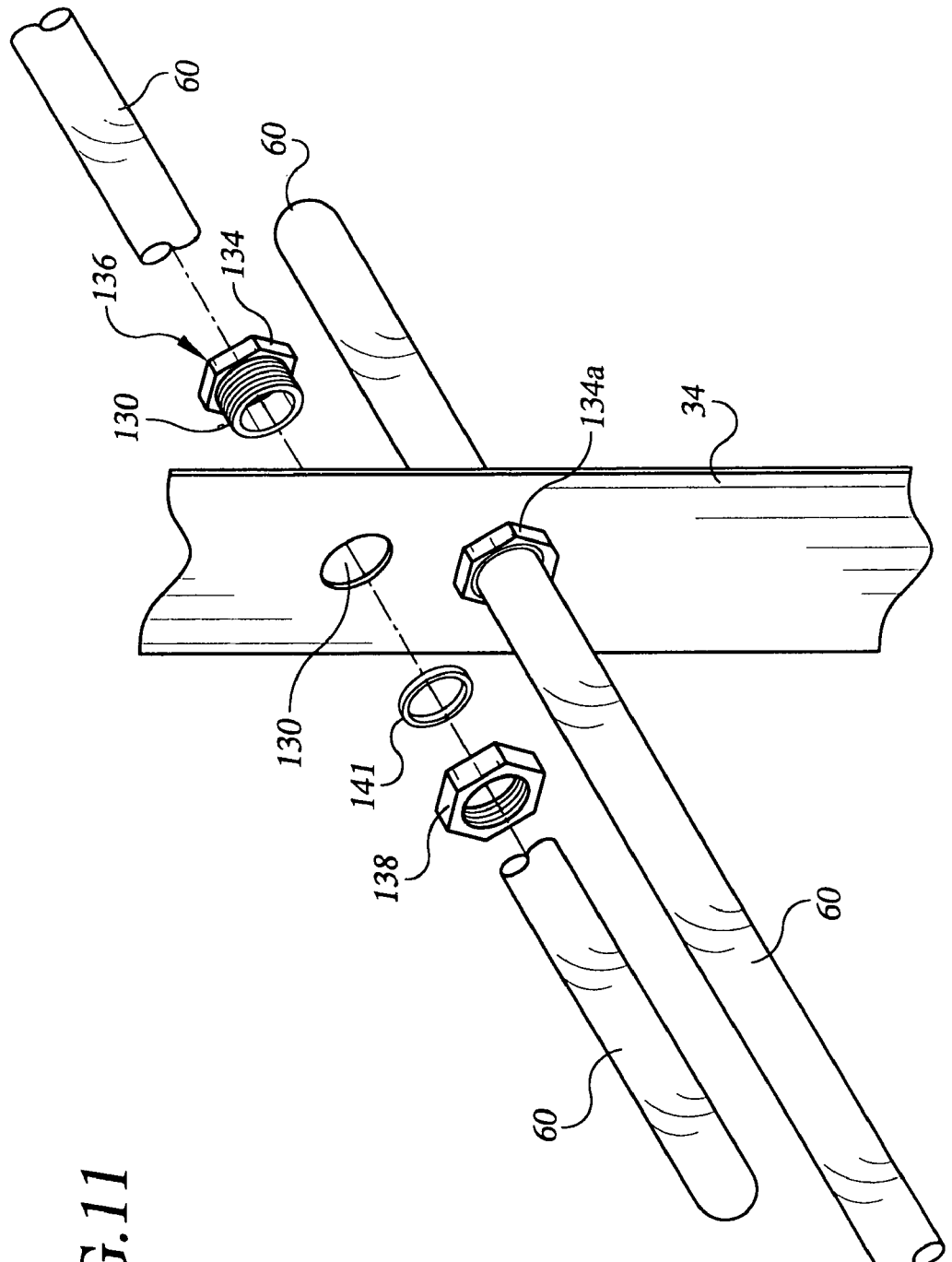
FIG. 11 is a partially exploded isometric view of detail E illustrated in FIG. 1.

As indicated hereinbefore, when it is desired to utilize longer length UV lamps within module 10, a cross support member may optionally be incorporated for adding rigidity and structural support to the framework-like configured module 10. The cross support member 34 illustrated in FIGS. 1, 8 and 11 is of an elongate rigid construction formed from metal or plastic and provided with a plurality of openings 128,128a to accommodate the slidable receipt therethrough of tubular support members 30,30a. Openings 130,130a are also provided for slidably receiving therethrough the corresponding quartz sleeves 60 of UV lamps 18 and 26, respectively, or simply the lamps themselves. As shown in greater detail in FIG. 8, openings 128,128a are sized to slidably receive therethrough exteriorly threaded annular extensions 132,132a emanating from a hexagonal-shaped nut 134,134a of compression fittings 136,136a, respectively. The annular compression fittings 136,136a, along with correspondingly threaded compression nuts 138,138a and compression rings 140,140a, are sized to be slidably mounted onto tubular support members 30,30a on either side of cross support member 34, and when it is desired to secure the cross support member in place to tubular support members 30,30a, compression rings 140,140a are placed over annular extensions 132,132a, respectively, followed by the mounting of compression nuts 138,138a thereto. The completed assembly is illustrated in FIG. 7.

As shown in FIGS. 9 and 11, cross support member 34 may also be secured to quartz sleeves 60 of UV lamps 18 and 26 in a similar fashion by securing compression nuts 138,138a to compression fittings 136,136a mounted about the quartz sleeves 60 on either side of cross support member 34. Instead of using compression rings 140,140a, which are usually made of metal for compression about tubular support members 30,30a, resilient O-rings 141 may be used for interfacing between the surface of quartz sleeve 60 and compression fittings 136,136a in the same as manner described for O-ring 56 used for securing the quartz sleeve/UV lamp assembly to housing 12 illustrated in FIG. 3. It is preferable that the resilient O-rings described herein be impervious to the deleterious effects of ultraviolet light, and as such can be of a Teflon® construction.

In the embodiment illustrated in FIG. 10, cross support member 35 may take the form of a channel when it is desired to utilize longer length UV lamps within module 10a. The ends of side walls 126 of cross member 35 are provided with an opening (not shown) that is in alignment with openings 120,121 of channel support members 114 and 116, respectively, so that the same threaded bolts 124 can be used to secure cross member 35 and channel support members 114 and 116 to each other. Openings identical to openings 130, 130a for cross support member 34 illustrated in FIGS. 8 and 11, along with locking devices in the form of compression fittings 136,136a and compression nuts 138,138a, are also provided in cross member 35 for the receipt therethrough and support of the quartz sleeve/UV lamp assemblies projecting from housings 12 and 20.

It will be understood that if quartz sleeves 60 are omitted from the air disinfection module, along with compression fittings 136,136a used to secure the quartz sleeves to cross support members 34 and 35 (see FIG. 11), the openings 130 in cross support members 34 and 35 will be in direct contact with the tubular portion 36 of UV lamps 18 and 26. Moreover, if cross support members 34 and 35 are of a metallic construction, such as aluminum or stainless steel, the contact of the lamp tubing with the metal cross support member may contribute to "cold spots" on the surface of the lamp's tubing which may lead to a condensation of mercury vapor in that area of contact with the lamp. Since ultraviolet light is created by the vaporization of the lamp's mercury, any compromise in vaporization will lead to an inefficient operation of the lamp and contribute to its shortened operating life.

As a result, and in place of compression fittings 136,136a, openings 130 in support members 34 and 35 may be provided with a resilient grommet whose construction is preferably impervious to the deleterious effects of ultraviolet light, e.g., EPDN (Viton®). The resilient grommet is configured for slidably receiving and maintaining in place UV lamps 18 and 26, and will typically have a slight resistance fit with the tubular portion 36 of the UV lamps for their stationary positioning relative to cross support members 34 or 35 as the case may be.

Figure 6:
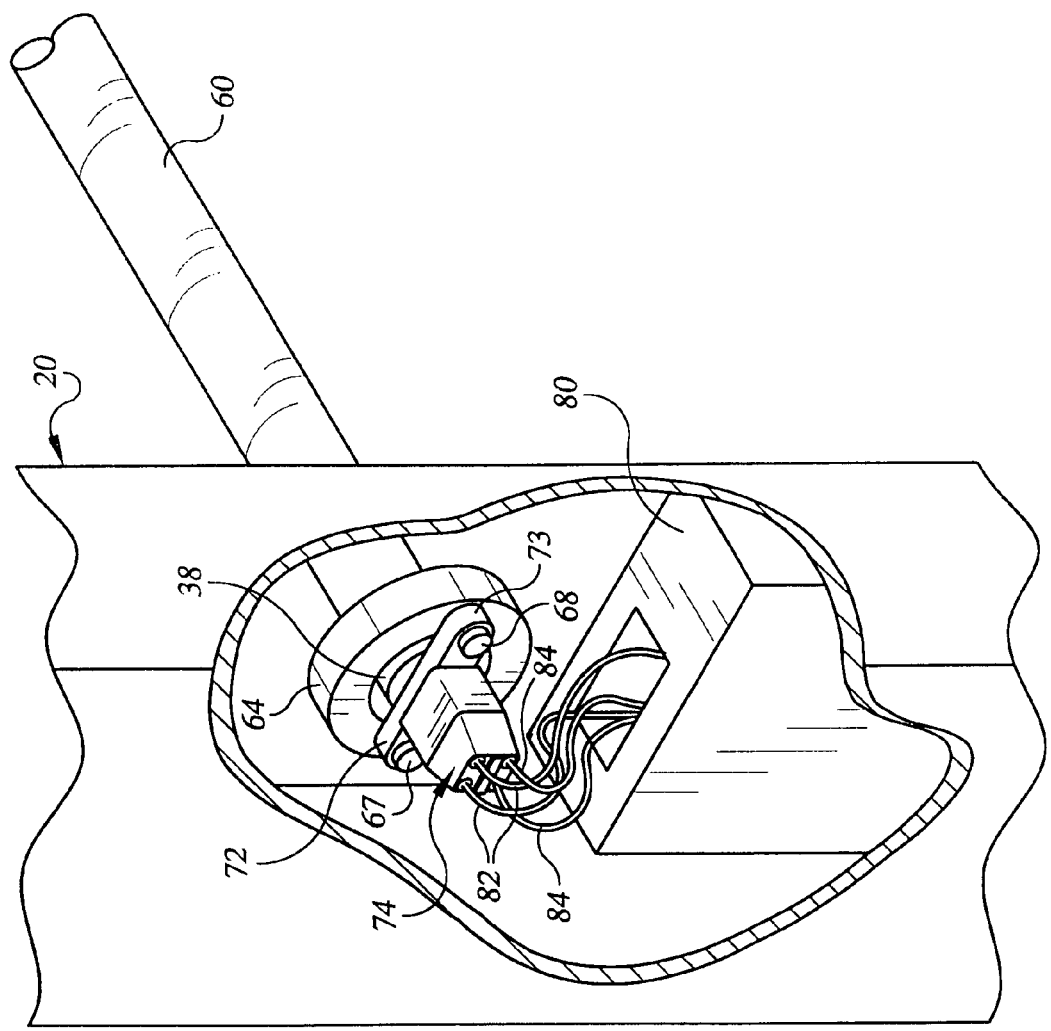
FIG. 6 is an enlarged isometric view of detail C illustrated in FIG. 1.

As illustrated in FIGS. 2, 4 and 6, the electrical terminal pins 48,50 of UV lamps 18 and 26 are electrically connected to one or more sources of electrical power, such as ballast 80, via electrical socket 74 provided with electrical wires 82 and 84. It will be appreciated that the longer length UV lamps can accommodate commercial duct sizes that are relatively large, usually encountered in large office buildings. Generally, for lamps greater than about 33 inches in length, one ballast will be required to power one lamp, but for UV lamps that are less than about 33 inches in length or much less, one ballast can supply power to two or more UV lamps depending on the size of the lamp. The electrical characteristics of the ultraviolet lamp and ballast should complement each other in order to contribute to the lamp's operational efficiency and longevity. In one embodiment, and for economy of space within a HVAC duct, it is desirable to position and fix the ballasts on or within the respective housings 12 and 20, preferably therein utilizing appropriate wiring or cables to connect the ballasts 80 to a power source exterior of modules 10 or 10a. The power source for connecting the wiring and cables is typically located exterior of the HVAC duct within which the fluid disinfection module is disposed.

Referring to FIG. 1, access to the interior of housings 12 and 20 may be gained by providing appropriate openings and/or removable covers therefor in the elongate side 17 opposite to side 16 of housing 12. A similar arrangement can be provided for housing 20. Alternatively, as shown in FIG. 1, the entire or partial length of elongate side 17 can be arranged in a "hinge" configuration with housing 12 whereby the respective entire or partial length of elongate edge 17a of elongate side 17 is hinged to the housing with hinges 17b to provide an access panel to the interior thereof.

Figure 12:
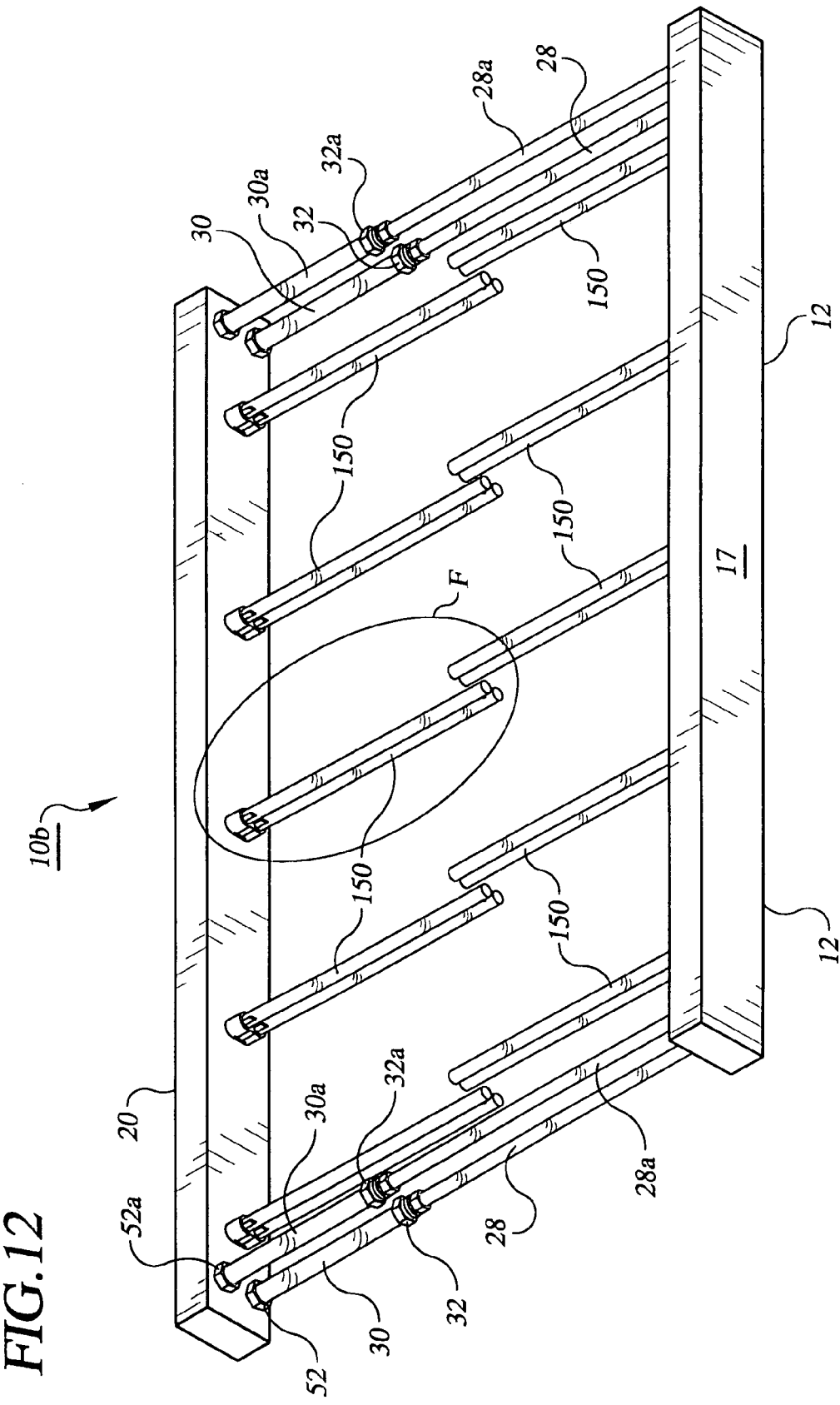
FIG. 12 is an isometric view of a fluid disinfection module according to another embodiment of the invention.

In place of the straight length UV lamps illustrated in FIGS. 1 and 2, or in combination therewith, "twin-tube" radiation sources can be utilized for formulating a fluid disinfection module 10b as illustrated in FIG. 12. Module 10b is essentially the same as module 10 with the exception that twin tube UV lamps 150 are utilized in place of the UV lamps 18 and 26 illustrated in FIG. 1. Moreover, because of the rigidity of twin tube UV lamps 150 and their manner of attachment to housings 12 and 20, no cross support member 34 is usually required for supporting these types of lamps. As shown in greater detail in FIG. 13, twin tube UV lamp 150, which may have a "hard glass" or "soft glass" construction, comprises two hollow elongate tubes 152,153 that are parallel to each other along their longitudinal lengths, and joined together about end portion 154 of lamp 150 by a short hollow connecting tube 155. The electrodes 157,158 of respective tubes 152,153 are disposed about end 156 opposite to end 154 of the lamp tubes, and are connected respectively, via lead wires (not shown), with terminal pins 159,160 disposed in and extending from a common lamp base 162. Lamp base 162 contains a slight indentation 163 in the top-middle and bottom-middle portions thereof to form respective lips 164 at the end of the lamp base 162. The lips 164 and terminal pins 159,160 are configured for engagement with corresponding catches 165 and terminal pin receptacles 167,168 of socket 170 which is mounted to elongate side 16 of housing 12 by the threaded engagement of threaded bolts 172, inserted through flanges 173 disposed on either side of socket 170, with openings 174 provided in elongate side 16 for that purpose. Elongate side 16 is provided with a rectangular opening 176 to accommodate the receipt therethrough of electrical transmission means in the form of connecting wires 178,179 leading from terminal pin receptacles 167,168, respectively, to a ballast (not shown) that may be located within or without housing 12 or disposed about another part of module 10b.

FIG. 14 illustrates another embodiment of a twin tube ultraviolet lamp in the form of U-shaped UV lamp 182 which closely resembles twin tube UV lamp 150. As the name implies, U-shaped UV lamp 182 has a U-shaped tubing portion 184 at the end of the lamp opposite to lamp base 170 that connects elongate tubes 152,153, and in all other respects is identical to twin tube UV lamp 150. As shown in FIG. 14, socket 170 has been mounted and secured to elongate side 16, and the terminal pins 159,160 projecting from lamp base 170 of U-shaped UV lamp 182 has been inserted into socket 170 for secure mounting of the lamp to housing 12. It will be appreciated that socket 170 can be mounted interiorly of housing 12 to the opposite side of elongate side 16 provided that an appropriate opening is provided in elongate side 16 for mounting the lamp to socket 170.

Figure 15:
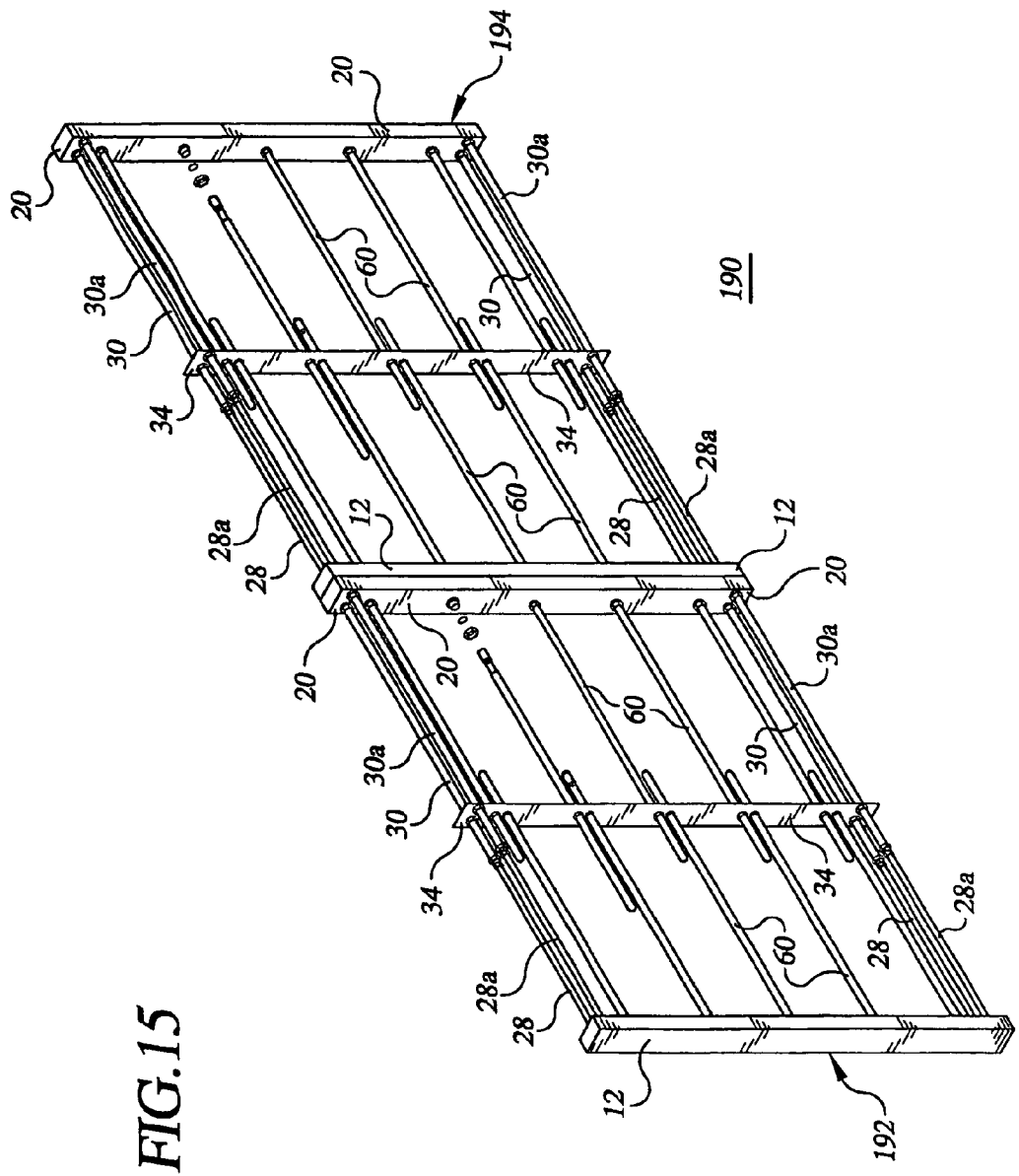
FIG. 15 is an isometric view of a pair of the fluid disinfection modules illustrated in FIG. 1, each module being assembled to each other to form an array in accordance with another embodiment of the invention.

In accordance with another embodiment of the invention, a multiplicity of modules 10, 10a and/or 10b can be used to form an array in which the modules are disposed and assembled laterally of each other. An array of modules, i.e., two or more, is generally used in the circumstance when the lengths of the UV lamps contained in a single module, e.g., module 10 illustrated in FIG. 1, and the resulting lateral distance x will not be sufficient for extending across the entire cross section of a given HVAC duct. Accordingly, in another aspect of the invention, and as shown in FIG. 15, an array 190 of two fluid disinfection modules 192 and 194 is formed by securing the adjacent housings of each module to each other, in this case, second housing 20 of module 192 and first housing 12 of module 194. These housings may be secured to each by any conventional means (not shown), for example, by using brackets or clamps, by securement to a common brace, rail or support, or by simply fastening the housings to each other using a nut/bolt arrangement or screws.

The array of modules may also include an arrangement whereby the individual modules are stacked, one over the other. In one embodiment, module 192 as shown in FIG. 15 will overlie the module 194, in which case, housing 12 of module 192 will overlie housing 12 of module 194. Another arrangement is to have housing 12 of module 192 overlie housing 20 of module 194, which in effect provides a lateral arrangement of the modules in which they are "staggered". In the latter arrangement, the overlapping of the housings 12 and 20 reduces the creation of any "blind" spaces within the HVAC duct to which the ultraviolet light emanating from UV lamps 18 and 26 would not be exposed to.

Figure 16:
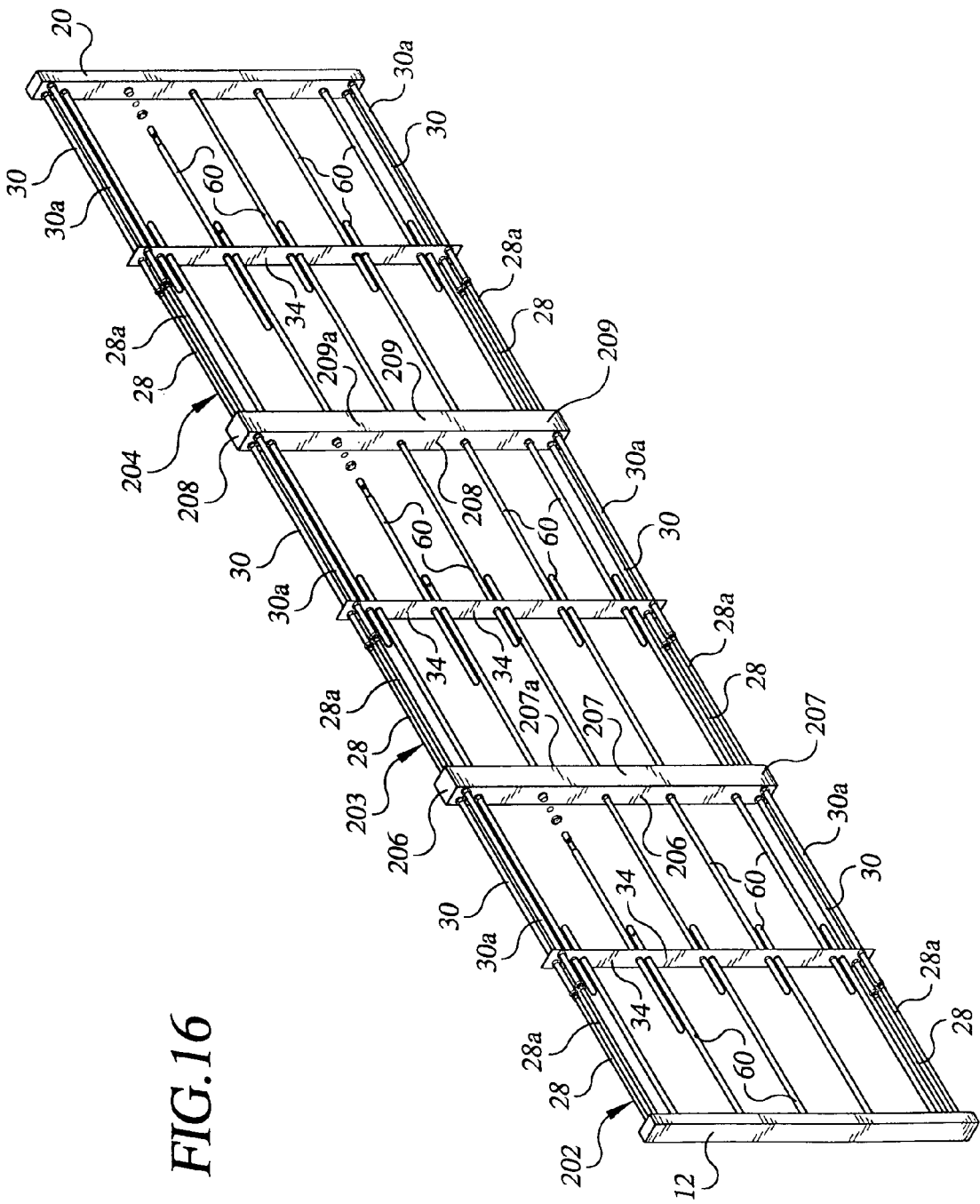
FIG. 16 is an isometric view of a plurality of the modules illustrated in FIG. 1, each module being assembled to each other with a common housing to form an array in accordance with yet another embodiment of the invention.

FIG. 16 illustrates another array 200 in which a greater number of fluid disinfection modules may be used to extend across exceptionally large ducts generally found in industrial plants and complexes. In the illustration shown, array 200 comprises three fluid disinfection modules 202, 203,204, although it will be understood that a greater number of modules may be utilized to formulate array 200 if circumstances warrant. Array 190 differs from array 200 in that air disinfection modules 202, 203 and 203, 204 share the same housings 206,208, respectively. In all other respects, modules 202,203, 204 are the same as module 10 illustrated in FIG. 1. Housing 206 has one end of tubular members 28,28a of module 203 secured to one side thereof with the opposite ends being slidably engaged and secured with tubular members 30,30a projecting from housing 208. In like manner, one end of tubular members 30,30a are secured to the opposite side of housing 206 while the opposite ends of tubular members 30,30a are slidably engaged and secured with tubular members 28,28a projecting from housing 12. Housing 208 has the same kind of arrangement. One end of tubular members 28,28a of module 204 are secured to and project from one side of housing 208 with the opposite ends of tubular members 28,28a being slidably engaged and secured with tubular members 30,30a projecting from housing 20. Cross support members 34 of modules 202,203,204 are engaged with and secured to tubular members 30,30a and quartz sleeves 60 in the same manner illustrated for module 10 in FIGS. 7, 8 and 11. Also, each of housings 206 and 208 receive and support either the UV lamp by itself or the UV lamp and protective sleeve assemblies on either sides thereof in the same manner illustrated for housings 12 and 20 in FIGS. 3, 4 and 5.

Inasmuch as housings 206,208 will contain an increased number of ballasts, electronics and wiring for powering both UV lamps 18 and 26, the physical capacity of these housings will be increased, either in the direction of the lateral plane of array 200 or in a direction perpendicular to the lateral plane. It is preferable to have the lateral width of housings 206 and 208 the same as housings 12 and 20 in order to avoid the creation of a space within the HVAC duct to which the ultraviolet light emanating from UV lamps 18 and 26 would not penetrate. Access to the increased size of housings 206,208 may be gained by arranging the entire or partial length of their respective elongate sides 207,209 in a "hinge" configuration whereby the respective entire or partial length of elongate edges 207a,209a of respective elongate sides 207,209 are hinged to housings 206,208 to provide an access panel to the interiors thereof.

The ultraviolet light modules or arrays thereof may be installed in a variety locations in a HVAC duct system depending on access thereto, preferably before or after the evaporator coils of the system's air conditioning unit(s). In addition, the modules or arrays may be stacked or placed in a series-type arrangement within the HVAC duct for treating the air passing therethrough.

The apparatus and module according to the invention herein also has application to systems other than the treatment of air. It may be used, for example, for the treatment of a fluid that includes wastewater or potable water passing through a conduit, provided that the necessary precautions are taken for water proofing the housings to protect the electronics contained therein and using protective sleeves for insulating the UV lamps from moisture.

Since other modifications and changes may be varied to fit the particular operating requirements and environments of the invention, which will be apparent to those skilled in the art, the invention is not considered to be limited to the embodiments chosen for purposes of disclosure, and covers all changes and modifications which do not constitute departures from the true spirit and scope thereof.

The invention claimed is:

1. An air disinfection module for use in a HVAC duct comprising a first enclosed housing and a second enclosed housing, said housings being arranged in laterally spaced-apart relationship to each other, each enclosed housing comprising a plurality of elongate tubular support structures extending laterally therefrom and joined with the corresponding elongate tubular support structures of the other housing for varying the lateral distance between said first and second enclosed housings, said first enclosed housing, second enclosed housing and corresponding elongate tubular support structures defining a framework structure for supporting a plurality of ultraviolet radiation sources detachably mounted to each of said enclosed housings, said ultraviolet radiation sources (i) projecting laterally from their corresponding housing towards the other housing; and (ii) communicating with one or more ballasts disposed within their respective enclosed housings.

2. The module according to claim 1 wherein each of said ultraviolet radiation sources is an ultraviolet lamp of a straight tubular construction comprising a lamp base disposed at one end thereof that includes electrical terminal pins mounted thereto.

3. The module according to claim 2 wherein said module additionally comprises a radiation pervious protective sleeve disposed about each ultraviolet lamp.

4. The module according to claim 3 wherein said radiation pervious protective sleeve is constructed of fused quartz.

5. The module according to claim 2 additionally comprising an electrical receptacle mounted to its respective housing for receiving therein the terminal pins of said lamp base.

6. The module according to claim 5 wherein the electrical receptacle is connected to at least one ballast for supplying electricity to said lamp.

7. The module according to claim 1 wherein said radiation source comprises an ultraviolet lamp having two, substantially parallel, tubular segments tubularly connected about one end thereof and terminating in a lamp base that is common to the two tubular segments, the lamp base being provided with electrical terminal pins mounted thereto.

8. The module according to claim 1 wherein the elongate tubular support structures of the first housing are mateably and slidably engaged with the tubular support structures of the second housing for varying the lateral distance between said first and second housings.

9. The module according to claim 8 wherein a plurality of the elongate support structures are disposed about each end of each of said housings.

10. The module according to claim 1 wherein the support structures of said first and second housings are detachably secured to each other by a locking device.

11. The module according to claim 10 wherein the locking device comprises a compression fitting disposed about each respective support structure of the first and second housings.

12. The module according to claim 11 wherein the elongate support structure of said first and second housings comprises an elongate channel member configured for slidable engagement of the first and second support structures with each other.

13. The module according to claim 12 wherein the elongate channel members of said first and second housings are detachably secured to each other.

14. The module according to claim 1 wherein each housing comprises a plurality of ballasts for supplying electricity to said ultraviolet radiation sources.

15. A first and second air disinfection module for use in a HVAC duct, said first and second modules being defined by claim 1 and wherein the first module is disposed laterally of the second module.

16. The first and second air disinfection modules according to claim 15 wherein the second housing of said first module is adjacent and secured to the first housing of said second module.

17. The first and second air disinfection modules according to claim 16 wherein the second housing of said first module and the first housing of said second module are common to each other.

18. The first and second air disinfection modules according to claim 15 wherein the first module overlies the second module.

19. A plurality of air disinfection modules, said modules being defined by claim 1, and wherein said modules are arranged laterally with respect to each other.

20. The plurality of air disinfection modules according to claim 19 wherein the first and second housings of the adjacent modules are common to each other.

21. An air disinfection module for use in a HVAC duct comprising a first enclosed housing and a second enclosed housing, said housings being arranged in laterally spaced-apart relationship to each other, each enclosed housing comprising a plurality of elongate, tubular support structures disposed about each end of each of said housings and extending laterally therefrom, said support structures being mateably and slidably engaged with the support structures of the other housing for varying the lateral distance between said first and second enclosed housings; said support structures of said first and second enclosed housings being detachably secured to each other by a locking device; and said first enclosed housing, second enclosed housing and corresponding elongate support structures defining a framework structure for supporting a plurality of ultraviolet radiation sources detachably mounted to each of said enclosed housings, said ultraviolet radiation sources (i) projecting laterally from their corresponding housing towards the other housing; (ii) communicating with one or more ballasts disposed within their respective enclosed housings; and (iii) additionally comprising a radiation pervious protective sleeve disposed about each radiation source.

22. The module according to claim 21 wherein the locking device comprises a compression fitting disposed about each respective support structure of the first and second housings.

23. The module according to claim 21 wherein the elongate support structures of said first and second housings comprise an elongate channel member configured for slidable engagement of the first and second support structures with each other.

24. The module according to claim 23 wherein the elongate channel members of said first and second housings are detachably secured to each other.

25. The module according to claim 21 wherein said radiation pervious protective sleeve is constructed of fused quartz.

26. The module according to claim 21 wherein each of said ultraviolet radiation sources comprises a lamp base disposed at one end thereof that includes electrical terminal pins mounted thereto.

27. The module according to claim 26 additionally comprising an electrical receptacle mounted to its respective housing for receiving therein the terminal pins of said lamp base.

* * * * *